United States Patent
Raines et al.

(10) Patent No.: US 9,630,916 B2
(45) Date of Patent: Apr. 25, 2017

(54) ORGANOCATALYSTS OF OXIDATIVE PROTEIN FOLDING

(71) Applicant: Wisconsin Alumni Research Foundation, Madison, WI (US)

(72) Inventors: Ronald T. Raines, Madison, WI (US); John C. Lukesh, III, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/830,357

(22) Filed: Aug. 19, 2015

(65) Prior Publication Data

US 2016/0052878 A1  Feb. 25, 2016

Related U.S. Application Data

(60) Provisional application No. 62/039,268, filed on Aug. 19, 2014.

(51) Int. Cl.
| | |
|---|---|
| C07C 233/36 | (2006.01) |
| C07C 233/78 | (2006.01) |
| C07C 271/20 | (2006.01) |
| C07C 323/60 | (2006.01) |
| C07C 327/06 | (2006.01) |
| C07K 14/00 | (2006.01) |
| B01J 31/02 | (2006.01) |

(52) U.S. Cl.
CPC ......... *C07C 327/06* (2013.01); *B01J 31/0217* (2013.01); *B01J 31/0237* (2013.01); *B01J 31/0247* (2013.01); *B01J 31/0271* (2013.01); *C07C 233/36* (2013.01); *C07C 233/78* (2013.01); *C07C 271/20* (2013.01); *C07C 323/60* (2013.01); *C07K 14/001* (2013.01); *B01J 31/0209* (2013.01); *B01J 31/0218* (2013.01)

(58) Field of Classification Search
CPC ... C07C 233/36; C07C 233/78; C07C 271/20; C07C 323/60; C07C 327/06; C07K 14/001
See application file for complete search history.

(56) References Cited

U.S. PATENT DOCUMENTS

| | | | |
|---|---|---|---|
| 4,659,733 | A | 4/1987 | DuPriest et al. |
| 4,755,528 | A | 7/1988 | DuPriest et al. |
| 5,651,960 | A | 7/1997 | Chan et al. |
| 5,910,435 | A | 6/1999 | Raines et al. |
| 9,090,662 | B2 | 7/2015 | Raines et al. |
| 9,371,521 | B2 | 6/2016 | Raines et al. |
| 2005/0002886 | A1 | 1/2005 | Philippe et al. |
| 2005/0019290 | A1 | 1/2005 | Philippe et al. |
| 2015/0307544 | A1 | 10/2015 | Raines et al. |

FOREIGN PATENT DOCUMENTS

WO  WO99/18196  4/1999

OTHER PUBLICATIONS

Ortega-Caballero et al., "Binding Affinity Properties of Dendritic Glycosides Based on a B-Cyclodextrin Core toward Guest Molecules and Concanavalin A," J. Org. Chem. 2001, 66, 7786-7795.*
Beld, J.; Woycechowsky, K. J.; Hilvert, D.(2007) "Selenoglutathione: Efficient Oxidative Protein Folding by a Diselenide," Biochemistry 46(18):4662-4662.
Beld, J.; Woycechowsky, K. J.; Hilvert, D. (2008) "Catalysis of Oxidative Protein Folding by Small-Molecule Diselenides," Biochemistry 47(27): 6985-6987.
Beld, J.; Woycechowsky, K. J.; Hilvert, D.(2009) "Erratum for Selenoglutathione: Efficient Oxidative Protein Folding by a Diselenide, Biochemistry 46(18):4662-4662," Biochemistry 48:4662.
Beld, J.; Woycechowsky, K. J.; Hilvert, D. (2010) "Diselenides as universal oxidative folding catalysts of diverse proteins," J. Biotechnol 150:481-489.
Blum, J. Bottcher, B. Sammet, T. Luksch, A. Heine, G. Klebe and W. E. Diederich (2008) "Achiral Oligoamines as Versatile Tool for the Development of Aspartic Protease Inhibitor," Bioorg. Med. Chem., 2008, 16, 8574-8586.
Cleland (1964) "Dithiothreitol: a new protective reagent for SH groups," Biochemistry. 3:480-482.
Gough, J. D.; Gargano, J. M.; Donofrio, A. E.; Lees, W. (2003) "Aromatic Thiol pKa Effects on the Folding Rate of a Disulfide Containing Protein," J. Biochemistry 42:11787-11797.
Gough, J. D.; Lees, W. J. (2005) "Effects of redox buffer properties on the folding of a disulfide-containing protein: dependence upon pH, thiol pKa, and thiol concentration," J. Biotechnol. 115: 279-290.
Gough, J. D.; Lees, W. J. (2005) "Increased catalytic activity of protein disulfide isomerase using aromatic thiol based redox buffers" Bioorg. Med. Chem. 15:777-781.

(Continued)

*Primary Examiner* — Paul A Zucker
*Assistant Examiner* — Mark Luderer
(74) *Attorney, Agent, or Firm* — Lathrop & Gage LLP

(57) ABSTRACT

Catalysts of protein-disulfide isomerization of formula:

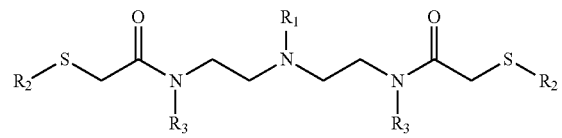

where $R_1$ is hydrogen or —$COR_4$, where $R_4$ is an optionally substituted aliphatic group or an optionally substituted aryl group; $R_2$ is hydrogen or —CO—$R_5$, where $R_5$ is alkyl having 1-8 carbon atoms, an alkenyl having 3-8 carbon atoms or a phenyl, benzyl, phenethyl or naphthyl group; and $R_3$ is hydrogen or alkyl group having 1-3 carbon atoms. Protein folding buffers comprising one or more of the above compounds. Method of catalyzing, in vivo or in vitro, the isomerization of disulfide linkages in a protein or peptide employing above catalysts. Method of forming, in vivo or in vitro, disulfide linkages in a protein or peptide employing above catalysts.

24 Claims, 5 Drawing Sheets

(56) References Cited

OTHER PUBLICATIONS

Gough, J. D.; Barrett, E. J.; Silva, Y.; Lees, W. J.(2006) "ortho- and meta-substituted aromatic thiols are efficient redox buffers that increase the folding rate of a disulfide-containing protein," J. Biotechnol 125:39-47.

Kessler et al. (1994) "Design and synthesis of a novel site-directed reducing agent for the disulfide bond involved in the acetylcholine binding site of the AChoR," Tetrahedron Letters. 35(39):7237-7240.

Lamoureux et al. (1993) "Synthesis of Dithiols as Reducing Agents for Disulfides in Neutral Aqueous Solutions and Comparison of Reduction Potentials," J. Org. Chem. 58:633-641.

Lees et al. (Dec. 1, 1991) "Meso-2,5-Dimercapto-N,N,N',N'-tetramethyladipamide: A readily available, kinetically rapid reagent for the reduction of disulfides in aqueous solution," J. Org. Chem. 56:7328-7331.

Lukesh, J.C. et al. (Feb. 2012) "A Potent, Versatile Disulfide-Reducing Agent from Aspartic Acid," J. Am. Chem. Soc. 134:4057-4059.

Lukesh, J.C. at al. (Oct. 2013) "Thiols and Selenols as Electron-Relay Catalysts for Disulfide Bond Reduction," Angew. Chem. Int Ed Rngl.:52(49):12901-12904.

Lukesh, J.C. et al. (Jul. 2014) "Pyrazine-derived disulfide-reducing agent for chemical biology," Chem. Comm 50:9591-9594.

Lukesh, J.C. et al (Sep. 2014) "Organocatalysts of oxidative protein folding inspired by protein disulfide isomerase," Org. Biomol. Chem. 12:8598-8602.

Patel, A. S.; Lees, W. J. (2012) "Oxidative folding of lysozyme with aromatic dithiols, and aliphatic and aromatic monothiol," Bioorg. Med. Chem. 20:1020-1028 available on-line Dec. 2011.

Singh et al. (1994) "Reagents for Rapid Reduction of Native Disulfide Bonds in Proteins," Bioorg. Chem. 22:109-115.

Singh, R.; Lamoureux, G. V.; Lees, W. J.; Whitesides, G. M. Methods Enzymol. 1995, 251, 167-173.

Vallejo, L.F. et al. (2004). Strategies for the recovery of active proteins through refolding of bacterial inclusion body proteins. Microbial Cell Factories 3:11-22.

Wang, G. Z.; Dong, X. Y.; Sun, Y. (Apr. 2011) "Peptide disulfides CGC and RKCGC facilitate oxidative protein refolding," Biochem. Eng. J. 55, 169-175.

Whitesides et al. (1977) "Rates of Thiol-Disulfide Interchange Reactions between Mono- and Dithiols and Ellman's Reagent," J. Org. Chem. 42:332-338.

Willis, M. S.; Hogan, J. K.; Prabhakar, P.; Liu, X.; Tsai, K.; Wei, Y.; Fox, T. (2005) Protein Sci. 14:1818-1826.

Woycechowsky KJ, Wittrup KD, Raines RT. (1999) "A small-molecule catalyst of protein folding in vitro and in vivo." Chem Biol. (12):871-9.

Woycechowsky KJ, Raines RT. (2000) "Native disulfide bond formation in proteins," Curr Opin Chem Biol. (5):533-9.

Woycechowsky KJ, Raines RT. (2003) "The CXC motif: a functional mimic of protein disulfide isomerase," Biochemistry. 42(18):5387-94.

Woycechowsky KJ, Hook BA, Raines RT. (2003) "Catalysis of protein folding by an immobilized small-molecule dithiol," Biotechnol Prog. (4):1307-14.

* cited by examiner

ORGANOCATALYSTS OF OXIDATIVE PROTEIN FOLDING

CROSS-REFERENCE TO RELATED APPLICATIONS

This application claims the benefit of U.S. provisional application 62/039,268, filed Aug. 19, 2014, which is incorporated by reference herein in its entirety.

STATEMENT REGARDING GOVERNMENT FUNDING

This invention was made with government support under GM044783 awarded by the National Institutes of Health. The government has certain rights in the invention.

BACKGROUND OF THE INVENTION

The formation of native disulfide bonds is at the core of oxidative protein folding. [1-4] In oxidizing environments, reduced proteins with multiple cysteine residues tend to oxidize rapidly and nonspecifically. To attain a proper three-dimensional fold, any non-native disulfide bonds must isomerize to the linkages found in the native protein. [5] In eukaryotic cells, this process is mediated by the enzyme protein disulfide isomerase (PDI; EC 5.3.4.1). [4,6-14]

Catalysis of disulfide-bond isomerization by PDI involves thiol-disulfide interchange chemistry (FIG. 1). [15] The mechanism commences with the nucleophilic attack by a thiolate on a non-native disulfide bond, generating a mixed-disulfide and a new substrate thiolate. This thiolate can then attack another non-native disulfide bond, inducing further rearrangements to achieve the stable native state (FIG. 1).

PDI is abundant in the endoplasmic reticulum (ER) of eukaryotic cells. The enzyme contains four domains: a, a', b, and b'. [12] The a and a' domains each contain one active-site CGHC motif—a pattern analogous to that in many other oxidoreductases, whereas the b and b' domains appear to mediate substrate binding. [16, 17, 12] The physicochemical properties of its active-site make PDI an ideal catalyst for the reshuffling of disulfide bonds in misfolded proteins. In its catalytic mechanism (FIG. 1), the deprotonated thiolate of the N-terminal active-site cysteine (C̲GHC) initiates catalysis. [18] The amount of enzymic thiolate present is dependent on two factors. [19,20] One is the $pK_a$ of the active-site cysteine residue; the other is the reduction potential ($E^{\circ\prime}$) of the disulfide bond formed between the two active-site cysteine residues. In PDI, the cysteine $pK_a$ is 6.7, and the disulfide $E^{\circ\prime}$ is −0.18 V. [21, 22] Given the properties of the ER (pH 7.0; $E_{solution}$=−0.18 V), about 33% of PDI active sites will contain a reactive thiolate. [23, 24] Moreover, the high (less negative) reduction potential of PDI renders the protein as a weak disulfide-reducing agent, ensuring that ample time is available for the catalyst to rearrange all of the disulfide bonds before reducing its protein substrate to "escape" (FIG. 1). If necessary, the second active-site cysteine residue can engage to rescue the enzyme from non-productive mixed-disulfide intermediates. [7, 25, 26]

Efficient oxidative protein folding requires a redox environment that supports both thiol oxidation and disulfide-bond isomerization. In vitro and in cellulo, this environment can be provided by a redox buffer consisting of reduced and oxidized glutathione. For example, the oxidative folding of a common model protein, bovine pancreatic ribonuclease (RNase A)[27, 84], occurs readily in the presence of 1 mM glutathione (GSH) and 0.2 mM oxidized glutathione (GSSG). [28] Adding PDI accelerates the process, but the large-scale use of PDI as a catalyst for folding proteins in vitro is impractical due to its high cost and conformational instability, and the complexity imposed by its separation from a substrate protein. Accordingly, the development of small-molecule PDI mimics has become a high priority.

To date, most PDI mimics have been designed to replicate the physicochemical properties of the CGHC active site with low thiol $pK_a$ and high disulfide $E^{\circ\prime}$. [29] For example, BMC, (±)-trans-1,2-bis(mercaptoacetamido)cyclohexane (FIG. 2), a small molecule that catalyzes the formation of native disulfide bonds in proteins, both in vitro and in vivo, has been reported. [30] U.S. Pat. No. 5,910,435 reports that organic dithiols, exemplified by BMC, having a pKa of less than about 8.0 and a standard reduction potential (EO') of greater than about −0.25 volts, are capable of catalyzing the formation of proper disulfide bonds in proteins, in the complete absence of PDI, both in vivo and in vitro. This patent also reports that BMC is capable both in vivo and in vitro of catalyzing the formation of the proper biologically active form of eukaryotic proteins produced in non-eukaryotic systems.

Fox and coworkers screened 14 reagents for their ability to fold a variety of proteins, and concluded that BMC was the best of known small-molecule catalysts. [31] Though effective, BMC has shortcomings. For example, its low disulfide $E^{\circ\prime}$ renders the compound too reducing for optimal catalysis of disulfide-bond isomerization. Subsequently, various CXXC and CXC peptides, aromatic thiols, and selenium-based catalysts have been reported to exhibit some success. [32-43] In addition to non-optimal thiol $pK_a$ and disulfide $E^{\circ\prime}$ values, these organocatalysts failed to mimic a hallmark of enzymic catalysts—binding to the substrate. [44] The b and b' domains of PDI have an exposed hydrophobic patch. These patches unite to form a continuous hydrophobic surface between the two active sites. [10, 12, 13, 45, 46] Unfolded or misfolded proteins tend to expose more hydrophobic residues than do proteins in their native fold. [47]

The present invention is directed to small molecule catalysts of disulfide bond formation and isomerization having improvements over art known catalysts.

SUMMARY OF THE INVENTION

The present invention provides small molecule catalysts of protein-disulfide isomerization having formula I:

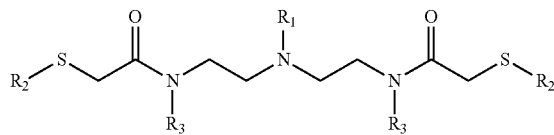

where:
$R_1$ is hydrogen or an acyl group —$COR_4$, where $R_4$ is an optionally substituted aliphatic group or an optionally substituted aryl group;
$R_2$ is hydrogen or an acyl group (—CO—$R_5$), where $R_5$ is alkyl having 1-8 carbon atoms, an alkenyl having 3-8 carbon atoms or a phenyl, benzyl, phenethyl or naphthyl group; and
$R_3$ is hydrogen or alkyl group having 1-3 carbon atoms.

Substituents for $R_4$, if present, are selected from halogens, alkyl groups having 1-6 carbon atoms, alkoxy groups having 1-6 carbon atoms and aryl groups having 6-12 carbon atoms.

In specific embodiments, all $R_2$ and $R_3$ are hydrogens. In specific embodiments, both $R_2$ are acyl group, where $R_5$ is an unsubstituted alkyl group having 1-3 carbon atoms. In specific embodiments, both $R_3$ are hydrogen. In specific embodiments, both $R_3$ are methyl groups.

In specific embodiments, $R_1$ is hydrogen. In other specific embodiments, $R_1$ is —$COR_4$.

In specific embodiments, $R_4$ groups are alkyl having 1-20 carbon atoms, alkenyl groups having 3-20 carbon atoms or an optionally substituted phenyl, biphenyl, indenyl, indanyl, benzyl, phenethyl, or naphthyl group. In specific embodiments, $R_4$ is an alicyclic group having 3-20 or 5-10 carbon atoms. In specific embodiments, $R_4$ is an alicyclic group having 3-10 or 5-10 carbon atoms. In specific embodiments, $R_4$ is a cyclopentyl, cyclohexyl, cyclooctyl, cyclononyl, cyclodecyl, cyclopentenyl, cyclohexenyl, cyclooctenyl, cyclononenyl or cyclodecenyl group. In specific embodiments, $R_4$ is a bicyclic or tricyclic alkyl or alkenyl group.

In specific embodiments, the $R_4$ group is unsubstituted.

In specific embodiments, $R_4$ is an alkyl or alkenyl group having 1-8 carbon atoms or an alkenyl group having 3-8 carbon atoms. In other specific embodiments, $R_4$ is an alkyl or alkenyl group having 2-8 carbon atoms or 2-6 carbon atoms. In other specific embodiments, $R_4$ is a cycloalkyl group having 5-10 carbon atoms. In other specific embodiments, $R_4$ is a branched alkyl group having 3-8 carbon atoms or 3-6 carbon atoms. In other specific embodiments, $R_4$ is a linear alkyl group having 1-8, 1-6, 2-8 or 2-6 carbon atoms. In other specific embodiments, $R_4$ is an alkenyl group having one or two double bonds other than a double bond alpha to the carbonyl in $R_1$. In other specific embodiments, $R_4$ is an alkenyl group having one double bond other than a double bond alpha to the carbonyl in $R_1$.

In specific embodiments, $R_4$ is an alkoxy substituted alkyl. In other specific embodiments, $R_4$ is a halogen substituted alkyl.

In a specific embodiment, $R_4$ is an alkyl group substituted with an aryl group. In other specific embodiments, $R_4$ is an alkyl group having 1-3 carbon atoms substituted with a phenyl group. In a specific embodiment, $R_4$ is an aryl group substituted with an alkyl group having 1-6 carbons.

In specific embodiments, $R_4$ is an aryl group. In specific embodiments, $R_4$ is and alkyl having 6-8 carbons. In specific embodiments, $R_4$ is an alkenyl group having 3-6 carbon atoms and one double bond where the double bonds in not adjacent to the —CO— moiety of the $R_1$ group. In specific embodiments, $R_4$ is an alkenyl group having 6-8 carbon atoms and one double bond where the double bonds in not adjacent to the —CO— moiety of the $R_1$ group.

In specific embodiments, $R_4$ is a phenyl group. In other specific embodiments, $R_4$ is a benzyl group. In other specific embodiments, $R_4$ is a phenethyl group (—$CH_2CH_2$—$C_6H_6$). In other specific embodiments, $R_4$ is an indenyl group. In other specific embodiments, $R_4$ is an indanyl group. In other specific embodiments, $R_4$ is an inden(1)yl group. In other specific embodiments, $R_4$ is a naphthyl group. In other specific embodiments, $R_4$ is a naphtha(1)yl group. In other specific embodiments, $R_4$ is a naphth(2)yl group.

In other specific embodiments, $R_4$ is an alkyl substituted phenyl. In other specific embodiments, $R_4$ is an alkoxy substituted phenyl. In other specific embodiments, $R_4$ is a halogen substituted phenyl. In other specific embodiments, $R_4$ is an alkyl substituted benzyl. In other specific embodiments, $R_4$ is an alkoxy substituted benzyl. In other specific embodiments, $R_4$ is a halogen substituted benzyl. In other specific embodiments, $R_4$ is an alkyl substituted phenethyl. In other specific embodiments, $R_4$ is an alkoxy substituted phenethyl. In other specific embodiments, $R_4$ is a halogen substituted phenethyl.

In specific embodiments, each $R_2$ and each of $R_3$ are hydrogens and $R_1$ is —$COR_4$, where $R_4$ is an unsubstituted straight-chain or branched alkyl group having 3-6 carbon atoms. In specific embodiments, each $R_2$ and each of $R_3$ are hydrogens and $R_1$ is —$COR_4$, where $R_4$ is a phenyl, benzyl, phenethyl, or an alkyl-substituted phenyl group. In specific embodiments, each $R_2$ and each $R_3$ are hydrogens and $R_1$ is —$COR_4$, where $R_4$ is an unsubstituted cycloalkyl group having 5-8 carbon atoms.

In specific embodiments each $R_2$ is —$COR_5$. In specific embodiments, each $R_2$ is —$COR_5$, each $R_3$ is hydrogen and $R_1$ is —$COR_4$. In more specific embodiments, $R_5$ is an alkyl group having 1-8 carbon atoms. In more specific embodiments, $R_5$ is an alkyl group having 1-3 carbon atoms. In more specific embodiments, $R_5$ is an alkenyl having 3-8 carbon atoms. In more specific embodiments, $R_5$ is a phenyl, benyl or phenethyl group.

In specific embodiments, the invention provides compounds useful in methods herein that are compounds of formula 1 with the exception that the compound is not compound 2. In specific embodiments, the invention provides compounds useful in methods herein that are compounds of formula 1 with the exception that the compound is not compound 3. In specific embodiments, the invention provides compounds useful in methods herein that are compounds of formula 1 with the exception that the compound is not compound 4.

In specific embodiments, compounds of the invention are compounds 4, 5, 6, 7, 8, 32, 33, 34, 35, 36 and 37 of FIG. 2.

Compounds of the invention of formula I are useful as catalysts for the formation of disulfide bonds, particularly for the formation of disulfide bonds in polypeptides and proteins.

The invention additionally provides protein folding buffers comprising one or more of the compounds of formula I. In specific embodiments, protein folding buffers are aqueous.

Compounds of the invention of formula I are useful as catalysts for the isomerization of disulfide bonds, particularly for the isomerization of disulfide bonds in polypeptides and proteins having at least one disulfide bond.

The invention provides a method of catalyzing the formation of disulfide linkages in a protein having non-native disulfide bonds to cause the protein to assume a biologically active conformation without the necessity for denaturation of the protein comprising contacting the protein with an amount of a compound of formula I effective for catalyzing the formation of a disulfide linkage in the protein. This method can be performed in vivo or in vitro.

The invention provides a method to form disulfide linkages in a protein to cause the protein to assume a biologically active conformation comprising contacting the protein with a compound of formula I. This method can be performed in vivo in a unicellular organism, e.g., a bacterium or yeast. In a specific embodiment, the protein is expressed in a heterologous host organism (e.g., a bacterium or yeast) and the compound of formula I is added to the medium in which the host organism is cultured.

The invention provides a method for facilitating the proper expression of a protein expressed in a heterologous host in which the protein may be expressed with non-native disulfide bonds comprising culturing the host under conditions favoring the expression of the protein in the host; and contacting the protein in vivo during the culturing step with an effective amount of a compound of formula I so as to cause a greater amount of the protein to assume a biologically active conformation than would be the case if the catalyst of formula I was not added. In a specific embodiment, the host is cultured under conditions favoring the expression of the protein in the host wherein at least some of the protein expressed includes a non-native disulfide bond.

DETAILED DESCRIPTION OF THE INVENTION

Figure 1:
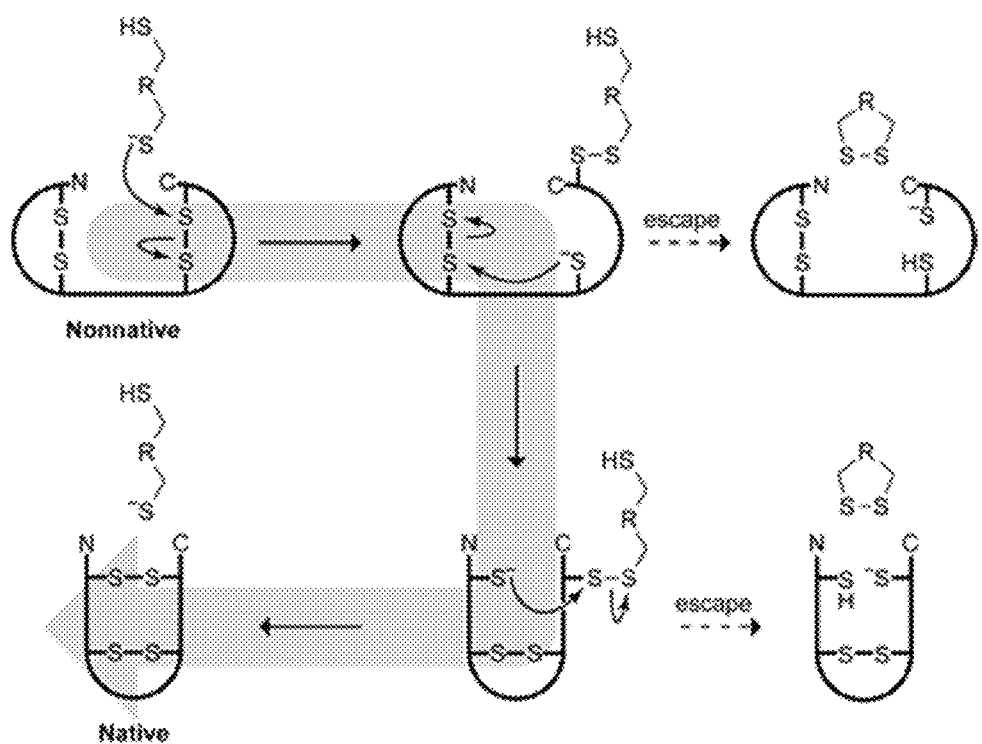
FIG. 1 illustrates the putatative mechanism for catalysis of protein-disulfide isomerization by protein disulfide isomerase (PDI) and small-molecule dithiol catalysts.

The invention relates to organocatalysts having low thiol $pK_a$ and high disulfide $E^{o\prime}$ values that also emulate substrate binding by PDI. This invention is based at least in part on the finding that certain dithiols carrying a hydrophobic group exhibit enhanced folding yield of proteins with non-native disulfide linkages and as such are useful catalysts of disulfide-bond isomerization and formation in polypeptides and proteins.

Organocatalysts of this invention include those of formula I:

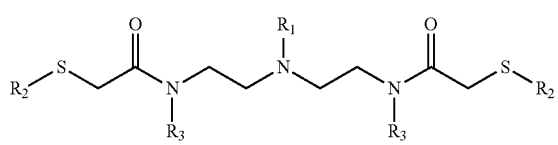

where:
$R_1$ is hydrogen or —COR$_4$ (an acyl group), where $R_4$ is an optionally substituted aliphatic group or an optionally substituted aryl group;
$R_2$ is hydrogen or —CO—R$_5$ (an acyl group), where $R_5$ is alkyl having 1-8 carbon atoms, an alkenyl having 3-8 carbon atoms or a phenyl, benzyl, phenethyl or naphthyl group, each of which is optionally substituted; and
$R_3$ is hydrogen or alkyl group having 1-3 carbon atoms.

Substituents for $R_4$, if present, are preferably selected from halogens, alkyl groups having 1-6 carbon atoms (more preferably methyl), alkoxy groups having 1-6 carbon atoms (more preferably methoxy) and aryl groups having 6-12 carbon atoms (more preferably phenyl, p-alkylphenyl, including p-methyl- and p-ethylphenyl).

In specific embodiments, all $R_2$ and $R_3$ are hydrogens. In specific embodiments, both $R_2$ are acyl groups, where $R_5$ is an unsubstituted alkyl group having 1-3 carbon atoms. In specific embodiments, both $R_3$ are hydrogens. In specific embodiments, both $R_3$ are methyl groups. In the forgoing embodiments, $R_1$ is hydrogen or —COR$_4$.

In specific embodiments, $R_1$ is hydrogen. In specific embodiments, $R_1$ is hydrogen and $R_2$ is hydrogen. In specific embodiments, $R_1$ is hydrogen and $R_2$ is —CO—R$_5$. In specific embodiments, $R_1$ is hydrogen and $R_2$ is —CO—R$_5$, where $R_5$ is an alkyl having 1-8 carbon atoms. In specific embodiments, $R_1$ is hydrogen and $R_2$ is —CO—R$_5$, where $R_5$ is an alkyl having 1-3 carbon atoms. In specific embodiments, $R_1$ is hydrogen and $R_2$ is —CO—R$_5$, where $R_5$ is an optionally substituted phenyl, benzyl, phenethyl or naphthyl group. In specific embodiments, $R_1$ is hydrogen and $R_2$ is —CO—R$_5$, where $R_5$ is an unsubstituted phenyl, benzyl, phenethyl or naphthyl group. In specific embodiments, $R_1$ is hydrogen and $R_2$ is —CO—R$_5$, where $R_5$ is a phenyl, benzyl, or phenethyl group. In specific embodiments, $R_1$ is hydrogen and $R_2$ is —CO—R$_5$, where $R_5$ is an alkyl substituted phenyl or benzyl group.

In specific embodiments, $R_1$ and each $R_3$ are hydrogens. In specific embodiments, $R_1$ and each $R_3$ are hydrogens and each $R_2$ is hydrogen. In specific embodiments, $R_1$ and each $R_3$ are hydrogens and each $R_2$ is —CO—R$_5$. In specific embodiments, $R_1$ and each $R_3$ are hydrogens and each $R_2$ is —CO—R$_5$, where $R_5$ is an alkyl having 1-8 carbon atoms. In specific embodiments, $R_1$ and each $R_3$ are hydrogens and each $R_2$ is —CO—R$_5$, where $R_5$ is an alkyl having 1-3 carbon atoms. In specific embodiment, $R_1$ and each $R_3$ are hydrogens and each $R_2$ is —CO—R$_5$, where $R_5$ is an optionally substituted phenyl, benzyl, phenethyl or naphthyl group. In specific embodiments, $R_1$ and each $R_3$ are hydrogens and each $R_2$ is —CO—R$_5$, where $R_5$ is an unsubstituted phenyl, benzyl, phenethyl or naphthyl group. In specific embodiments, $R_1$ and each $R_3$ are hydrogens and each $R_2$ is —CO—R$_5$, where $R_5$ is a phenyl, benzyl, or phenethyl group. In specific embodiments, $R_1$ and each $R_3$ are hydrogens and each $R_2$ is —CO—R$_5$, where $R_5$ is an alkyl substituted phenyl or benzyl group.

In specific embodiments, $R_1$ is hydrogen, each $R_2$ is hydrogen and each $R_3$ is hydrogen.

In specific embodiments, $R_1$ is —COR$_4$. In specific embodiments, $R_1$ is —COR$_4$. In specific embodiments, $R_1$ is —COR$_4$ and each $R_2$ is hydrogen. In specific embodiments, $R_1$ is —COR$_4$ and each $R_2$ is —CO—R$_5$. In specific embodiments, $R_1$ is —COR$_4$ and each $R_2$ is —CO—R$_5$, where $R_5$ is an alkyl having 1-8 carbon atoms. In specific embodiments, $R_1$ is —COR$_4$ and each $R_2$ is —CO—R$_5$, where $R_5$ is an alkyl having 1-3 carbon atoms. In specific embodiments, $R_1$ is —COR$_4$ and each $R_2$ is —CO—R$_5$, where $R_5$ is an optionally substituted phenyl, benzyl, phenethyl or naphthyl group. In specific embodiments, $R_1$ is —$COR_4$ and each $R_2$ is —CO—$R_5$, where $R_5$ is an unsubstituted phenyl, benzyl, phenethyl or naphthyl group. In specific embodiments, $R_1$ is —$COR_4$ and each $R_2$ is —CO—$R_5$, where $R_5$ is a phenyl, benzyl, or phenethyl group. In specific embodiments, $R_1$ is —$COR_4$ and each $R_2$ is —CO—$R_5$, where $R_5$ is an alkyl substituted phenyl or benzyl group.

In specific embodiments, $R_1$ is —$COR_4$ and each $R_3$ is hydrogen. In specific embodiments, $R_1$ is —$COR_4$ and each $R_3$ is hydrogen and each $R_2$ is hydrogen. In specific embodiments, $R_1$ is —$COR_4$ and each $R_3$ is hydrogen and each $R_2$ is —CO—$R_5$. In specific embodiments, $R_1$ is —$COR_4$ and each $R_3$ is hydrogen and each $R_2$ is —CO—$R_5$, where $R_5$ is an alkyl having 1-8 carbon atoms. In specific embodiments, $R_1$ is —$COR_4$ and each $R_3$ is hydrogen and each $R_2$ is —CO—$R_5$, where $R_5$ is an alkyl having 1-3 carbon atoms. In specific embodiment, $R_1$ is —$COR_4$ and $R_3$ is hydrogen and each $R_2$ is —CO—$R_5$, where $R_5$ is an optionally substituted phenyl, benzyl, phenethyl or naphthyl group. In specific embodiments, $R_1$ is —$COR_4$ and $R_3$ is hydrogen and $R_2$ is —CO—$R_5$, where $R_5$ is an unsubstituted phenyl, benzyl, phenethyl or naphthyl group. In specific embodiments, $R_1$ is —$COR_4$ and each $R_3$ is hydrogen and each $R_2$ is —CO—$R_5$, where $R_5$ is a phenyl, benzyl, or phenethyl group. In specific embodiments, $R_1$ is —$COR_4$ and $R_3$ is hydrogen and each $R_2$ is —CO—$R_5$, where $R_5$ is an alkyl substituted phenyl or benzyl group.

$R_2$ groups in formula I may be the same groups or different groups. Preferably the $R_2$ groups in formula I are the same.

$R_3$ groups in formula I may be the same of different groups. Preferably the $R_3$ groups in formula I are the same.

In specific embodiments, when $R_1$ is —$COR_4$, $R_4$ groups are alkyl having 1-20 carbon atoms, or alkenyl groups having 3-20 carbon atoms. In other embodiments, $R_4$ groups are phenyl, biphenyl, indenyl, indanyl, benzyl, phenethyl, or naphthyl groups. In specific embodiments, $R_4$ groups are alkyl having 1-20 carbon atoms, or alkenyl groups having 3-20 carbon atoms which are optionally substituted, wherein optional substitution includes substitution with one or more halogens, alkyl groups, or alkoxy groups. In specific embodiments, $R_4$ groups are alkyl having 1-20 carbon atoms. In specific embodiments, $R_4$ groups are alkyl having 1-8 carbon atoms. In specific embodiments, $R_4$ groups are alkyl having 1-6 carbon atoms. In specific embodiments, $R_4$ groups are alkyl having 3-6 carbon atoms. In specific embodiments, $R_4$ groups are alkyl having 3-8 carbon atoms. In specific embodiments, $R_4$ groups are alkenyl groups having 3-20 carbon atoms. In specific embodiments, $R_4$ groups are alkyl groups having 1-20 carbon atoms which are substituted with one or more halogens, alkyl groups, or alkoxy groups. In other embodiments, $R_4$ groups are phenyl, biphenyl, indenyl, indanyl, benzyl, phenethyl, or naphthyl groups optionally substituted with substitution with one or more halogens, alkyl groups, or alkoxy groups. In specific embodiments, $R_4$ groups are unsubstituted phenyl, biphenyl, indenyl, indanyl, benzyl, phenethyl, or naphthyl groups. In specific embodiments, $R_4$ is an alicyclic group having 3-20 or 5-10 carbon atoms. In specific embodiments, $R_4$ is an alicyclic group having 3-10 or 5-10 carbon atoms. In specific embodiments, $R_4$ is a cyclopentyl, cyclohexyl, cyclooctyl, cyclononyl, cyclodecyl, cyclopentenyl, cyclohexenyl, cyclooctenyl, cyclononenyl or cyclodecenyl group. In specific embodiments, $R_4$ is a bicyclic or tricyclic alkyl or alkenyl group. In the forgoing embodiments, each $R_2$ is hydrogen or each $R_2$ is —$COR_5$ or each $R_3$ is hydrogen or each $R_3$ is a methyl group.

In specific embodiments, the $R_4$ group is unsubstituted. In specific embodiments, $R_4$ is unsubstituted phenyl. In specific embodiments, $R_4$ is unsubstituted benzyl. In specific embodiments, $R_4$ is unsubstituted phenethyl. In specific embodiments, $R_4$ is p-alkyl substituted phenyl, benzyl or phenethyl. In specific embodiments, $R_4$ is p-alkyl substituted phenyl. In specific embodiments, $R_4$ is phenyl substituted with an alkyl group having 1-3 carbon atoms in the p-position. In the forgoing embodiments, each $R_2$ is hydrogen or each $R_2$ is —$COR_5$ or each $R_3$ is hydrogen or each $R_3$ is a methyl group.

In specific embodiments, $R_4$ is an alkyl or alkenyl group having 1-8 carbon atoms or an alkenyl group having 3-8 carbon atoms. In other specific embodiments, $R_4$ is an alkyl or alkenyl group having 2-8 carbon atoms or 2-6 carbon atoms. In other specific embodiments, $R_4$ is a cycloalkyl group having 5-10 carbon atoms. In other specific embodiments, $R_4$ is a branched alkyl group having 3-8 carbon atoms or 3-6 carbon atoms. In other specific embodiments, $R_4$ is a linear alkyl group having 1-8, 1-6, 2-8 or 2-6 carbon atoms. In other specific embodiments, $R_4$ is an alkenyl group having one or two double bonds other than a double bond alpha to the carbonyl in $R_1$. In other specific embodiments, $R_4$ is an alkenyl group having one double bond other than a double bond alpha to the carbonyl in $R_1$. In the forgoing embodiments, each $R_2$ is hydrogen or each $R_2$ is —$COR_5$ or each $R_3$ is hydrogen or each $R_3$ is a methyl group.

In specific embodiments, $R_4$ is an alkoxy substituted alkyl. In other specific embodiments, $R_4$ is a halogen substituted alkyl. In the forgoing embodiments, each $R_2$ is hydrogen or each $R_2$ is —$COR_5$ or each $R_3$ is hydrogen or each $R_3$ is a methyl group.

In a specific embodiment, $R_4$ is an alkyl group substituted with an aryl group. In other specific embodiments, $R_4$ is an alkyl group having 1-3 carbon atoms substituted with a phenyl group. In a specific embodiment, $R_4$ is an aryl group substituted with an alkyl group having 1-6 carbons. In the forgoing embodiments, each $R_2$ is hydrogen or each $R_2$ is —$COR_5$ or each $R_3$ is hydrogen or each $R_3$ is a methyl group.

In specific embodiments, $R_4$ is an aryl group. In specific embodiments, $R_4$ is and alkyl having 6-8 carbons. In specific embodiments, $R_4$ is an alkenyl group having 3-6 carbon atoms and one double bond where the double bonds in not adjacent to the —CO— moiety of the $R_1$ group. In specific embodiments, $R_4$ is an alkenyl group having 6-8 carbon atoms and one double bond where the double bonds in not adjacent to the —CO— moiety of the $R_1$ group. In the forgoing embodiments, each $R_2$ is hydrogen or each $R_2$ is —$COR_5$ or each $R_3$ is hydrogen or each $R_3$ is a methyl group.

In specific embodiments, $R_4$ is a phenyl group. In other specific embodiments, $R_4$ is a benzyl group. In other specific embodiments, $R_4$ is a phenethyl group (—$CH_2CH_2$—$C_6H_6$). In other specific embodiments, $R_4$ is an indenyl group. In other specific embodiments, $R_4$ is an indanyl group. In other specific embodiments, $R_4$ is an inden(1)yl group. In other specific embodiments, $R_4$ is a naphthyl group. In other specific embodiments, $R_4$ is a naphtha(1)yl group. In other specific embodiments, $R_4$ is a naphth(2)yl group. In the forgoing embodiments, each $R_2$ is hydrogen or each $R_2$ is —$COR_5$ or each $R_3$ is hydrogen or each $R_3$ is a methyl group.

In other specific embodiments, $R_4$ is an alkyl substituted phenyl. In other specific embodiments, $R_4$ is an alkoxy substituted phenyl. In other specific embodiments, $R_4$ is a halogen substituted phenyl. In other specific embodiments, $R_4$ is an alkyl substituted benzyl. In other specific embodiments, $R_4$ is an alkoxy substituted benzyl. In other specific embodiments, $R_4$ is a halogen substituted benzyl. In other specific embodiments, $R_4$ is an alkyl substituted phenethyl. In other specific embodiments, $R_4$ is an alkoxy substituted phenethyl. In other specific embodiments, $R_4$ is a halogen substituted phenethyl. In the forgoing embodiments, each $R_2$ is hydrogen or each $R_2$ is —$COR_5$ or each $R_3$ is hydrogen or each $R_3$ is a methyl group.

In specific embodiments, the invention provides compounds useful in methods herein that are compounds of formula 1 with the exception that the compound is not compound 2. In specific embodiments, the invention provides compounds useful in methods herein that are compounds of formula 1 with the exception that the compound is not compound 3. In specific embodiments, the invention provides compounds useful in methods herein that are compounds of formula 1 with the exception that the compound is not compound 4. In specific embodiments, the invention provides compounds useful in methods herein that are compounds of formula 1 with the exception that the compound is not compound 5. In specific embodiments, the invention provides compounds useful in methods herein that are compounds of formula 1 with the exception that the compound is not compound 6. In specific embodiments, the invention provides compounds useful in methods herein that are compounds of formula 1 with the exception that the compound is not compound 7. In specific embodiments, the invention provides compounds useful in methods herein that are compounds of formula 1 with the exception that the compound is not compound 8.

In specific embodiments, the invention provides compounds useful in methods herein that are compounds of formula 1 with the exception that the compound is not compound 32. In specific embodiments, the invention provides compounds useful in methods herein that are compounds of formula 1 with the exception that the compound is not compound 33. In specific embodiments, the invention provides compounds useful in methods herein that are compounds of formula 1 with the exception that the compound is not compound 34. In specific embodiments, the invention provides compounds useful in methods herein that are compounds of formula 1 with the exception that the compound is not compound 35. In specific embodiments, the invention provides compounds useful in methods herein that are compounds of formula 1 with the exception that the compound is not compound 36. In specific embodiments, the invention provides compounds useful in methods herein that are compounds of formula 1 with the exception that the compound is not compound 37.

Figure 2:
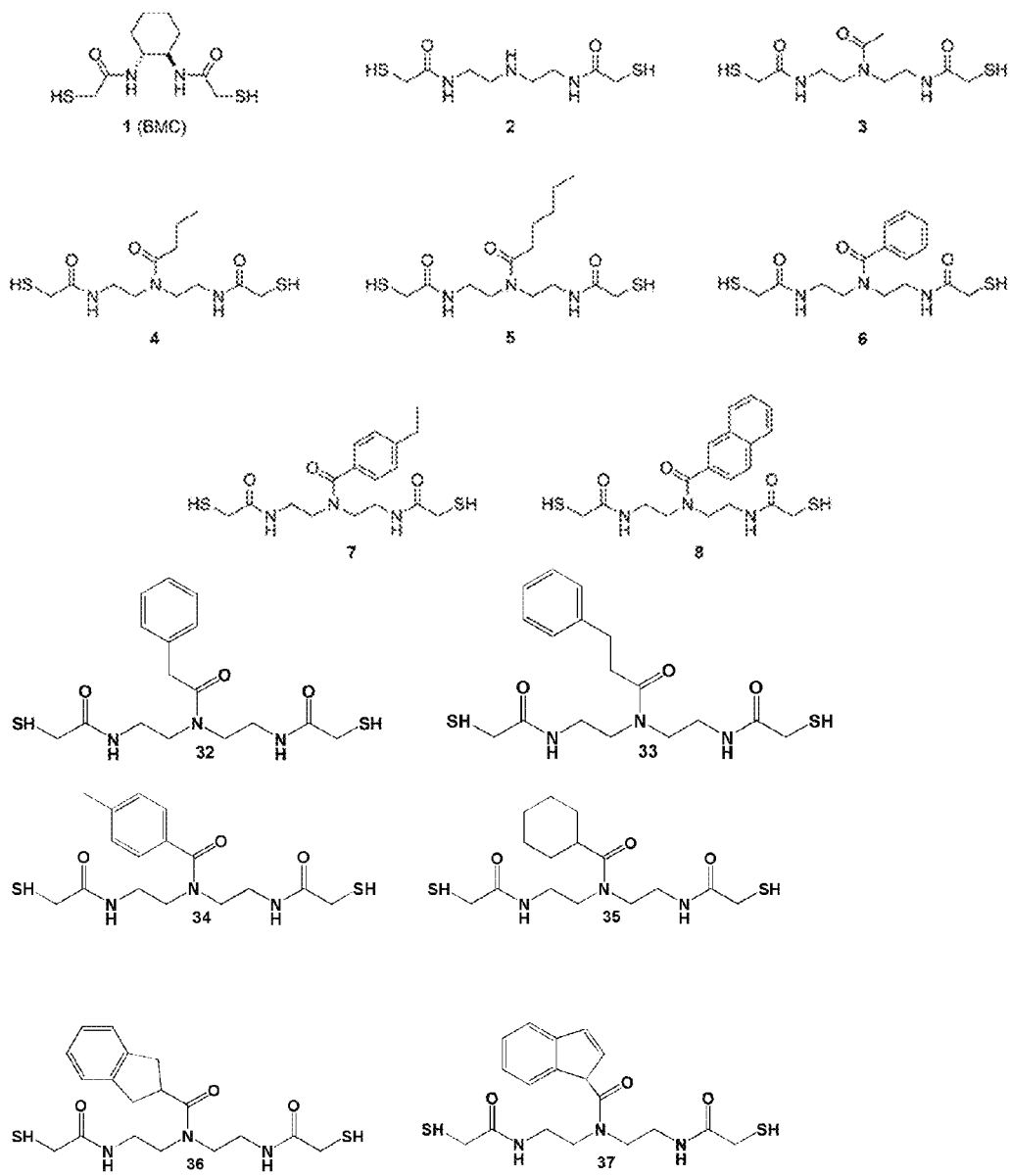
FIG. 2 illustrates exemplary small-molecule PDI mimics.

In specific embodiments, compounds of the invention are compounds 4, 5, 6, 7, 8, 32, 33, 34, 35, 36 or 37 of FIG. 2.

Compounds of the invention in all the forgoing embodiments are useful as catalysts for the formation of disulfide bonds, particularly for the formation of disulfide bonds in polypeptides and proteins.

The invention additionally provides protein folding buffers comprising one or more of the compounds of any of the forgoing embodiments. In specific embodiments, protein folding buffers are aqueous.

Compounds of the invention in all the forgoing embodiments are useful as catalysts for the isomerization of disulfide bonds, particularly for the isomerization of disulfide bonds in polypeptides and proteins having at least one disulfide bond.

The invention provides a method of catalyzing the formation of disulfide linkages in a protein having non-native disulfide bonds to cause the protein to assume a biologically active conformation without the necessity for denaturation of the protein comprising contacting the protein with an amount of a compound of the invention or any of the forgoing embodiments effective for catalyzing the formation of a disulfide linkage in the protein. These method can be performed in vivo or in vitro.

The invention provides a method to form disulfide linkages in a protein to cause the protein to assume a biologically active conformation comprising contacting the protein with one or more compounds of formula I. This method can be performed in vivo in a unicellular organism, e.g., a bacterium or yeast. In a specific embodiment, the protein is expressed in a heterologous host organism (e.g., a bacterium or yeast) and the one or more compounds of formula I is added to the medium in which the host organism is cultured. More specifically, the invention provides a method to form disulfide linkages in a protein to cause the protein to assume a biologically active conformation comprising contacting the protein with one or more compounds of any of the forgoing embodiments. This method can be performed in vivo in a unicellular organism, e.g., a bacterium or yeast. In a specific embodiment, the protein is expressed in a heterologous host organism (e.g., a bacterium or yeast) and the one or more compounds of any of the forgoing embodiments is added to the medium in which the host organism is cultured.

The invention provides a method for facilitating the proper expression of a protein expressed in a heterologous host in which the protein may be expressed with non-native disulfide bonds comprising culturing the host under conditions favoring the expression of the protein in the host; and contacting the protein in vivo during the culturing step with an effective amount (or a combined effective amount) of one or more compounds of formula I so as to cause a greater amount of the protein to assume a biologically active conformation than would be the case if the one or more compounds of formula I was not added. In a specific embodiment, the host is cultured under conditions favoring the expression of the protein in the host wherein at least some of the protein expressed includes a non-native disulfide bond. The invention provides a method for facilitating the proper expression of a protein expressed in a heterologous host in which the protein may be expressed with non-native disulfide bonds comprising culturing the host under conditions favoring the expression of the protein in the host; and contacting the protein in vivo during the culturing step with an effective amount (or a combined effective amount) of one or more compounds of any of the forgoing embodiments so as to cause a greater amount of the protein to assume a biologically active conformation than would be the case if the one or more compounds of the forgoing embodiments was not added.

Dithiol 2 (FIG. 2) was chosen as a scaffold for the development of useful catalysts. The mercaptoacetamido groups of this dithiol are known to have low thiol $pK_a$ values. [54, 30] The disulfide bonds of the oxidized form of this dithiol reside in a large, 13-membered ring containing two secondary amides, which could lead to a high reduction potential. Finally, dithiol 2 has an amino group that can be condensed with hydrophobic carboxylic acids to mimic the b and b' domains of PDI.

Dithiol 2 was synthesized from diethylenetriamine in a few high-yielding steps (see: The Examples). Thiol $pK_a$ values were measured by monitored the thiols $A_{238\ am}$ as a function of pH. [30, 55] Thiol $pK_a$ values of 8.0±0.2 and 9.2±0.1 were measured for dithiol 2 (Table 1). These values are slightly less than those of BMC (Table 1), presumably due to the introduction of an additional electronegative nitrogen atom. To determine the reduction potential of the oxidized form of the dithiol, equimolar amounts of dithiol 2 and oxidized β-mercaptoethanol were equilibrated and the amount of each reduced and oxidized species was quantitated with analytical HPLC. [56, 30] The disulfide $E^{\circ\prime}$ value for dithiol 2 was found to be (−0.192±0.003) V. This value indicates that dithiol 2 is a weaker reducing agent than is BMC, which is consistent with BMC being more preorganized for disulfide-bond formation. Finally, to probe the effect of increasing hydrophobicity on catalyzing the formation of native disulfide bonds in proteins, dithiols 3-8 were synthesized.

Figure 3:
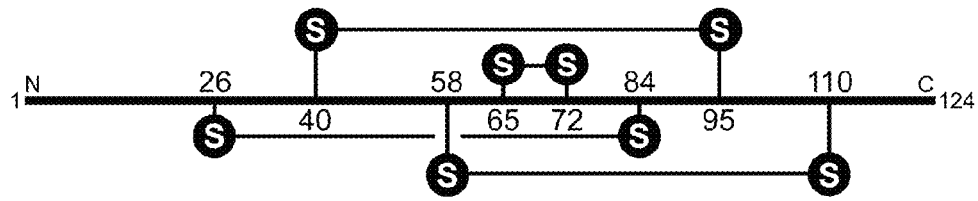
FIG. 3 illustrates a scheme showing the connectivity of the four disulfide bonds in native RNase A. There are 104 other fully oxidized forms.

Enzymatic catalysis provides an extremely sensitive measure of native protein structure. [57] RNase A contains eight cysteine residues, which could form 105 (=7×5×3×1) distinct fully oxidized species, only one of which gives rises to enzymatic activity (FIG. 3). [27] Accordingly, the ability of this panel of compounds to catalyze the isomerization of "scrambled" RNase A (sRNase A) was tested. "Scrambled" RNase A is a random mixture of oxidized species, compared to its native state. The isomerization reaction was monitored by measuring the gain of catalytic activity. [58]

Figure 4A:
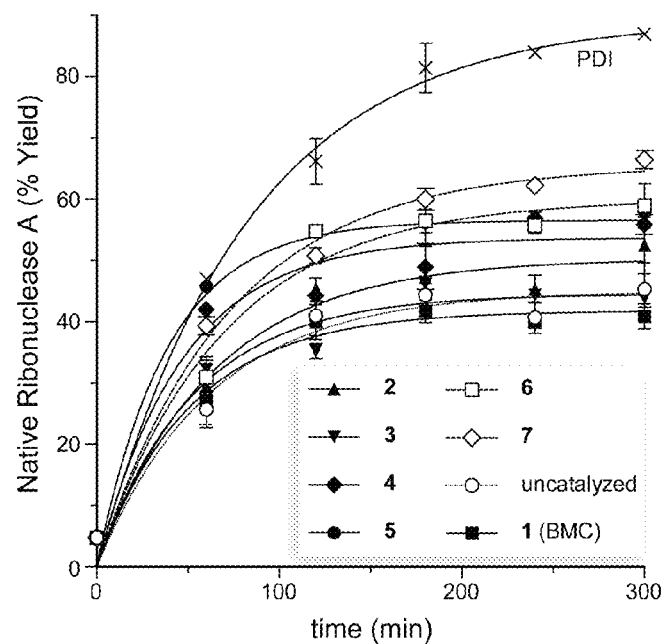
FIGS. 4A and 4B are graphs illustrating catalysis of disulfide-bond isomerization by PDI and PDI mimics 1-7. (4A) Is a graph of the time-course for the unscrambling of sRNase A to give native RNase A. All reactions were performed at 30° C. in 50 mM Tris-HCl buffer, pH 7.6, containing GSH (1.0 mM), GSSG (0.2 mM), and PDI or dithiol 1-7 (1.0 mM). (4B) Is a graph of yield of native RNase A achieved by PDI mimics 2-7 after 5 h as a function of the calculated log P values listed in Table 1.
Figure 4B:
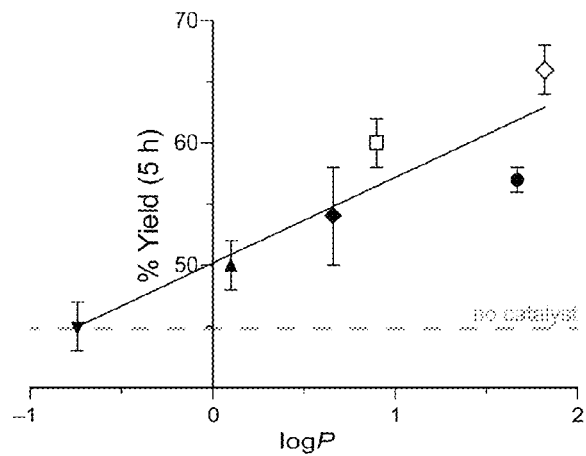

Some, but not all, of the PDI mimics led to a significant increase in the yield of oxidative protein folding (FIG. 4A). Most notably, the data with dithiols 2-7 revealed an overall trend toward higher yield with increasing hydrophobicity of the pendant carboxamide (FIG. 4B). This trend culminated with dithiol 7, which increased the yield of folded RNase A by 47% versus the uncatalyzed reaction. Notably, our data contrast with the properties of monothiols (e.g., glutathione), which have been shown to reduce the yield of properly folded protein by favoring the accumulation of mixed-disulfide species. [28]

The apparent correlation of catalytic efficacy with hydrophobicity could be due to a physicochemical property other than hydrophobicity. Accordingly, the thiol $pK_a$ and disulfide $E^{\circ\prime}$ values of the efficacious dithiols containing an alkyl (5) and aryl (7) carboxamide were determined. Dithiol 5 was found to have thiol $pK_a$ values of 8.1 and 9.3 and a disulfide $E^{\circ\prime}$ value of −0.203 V (Table 1). Dithiol 7 was found to have similar physicochemical properties, with thiol $pK_a$ values of 8.1 and 9.4 and a disulfide $E^{\circ\prime}$ value of −0.206 V. Both of these compounds possess thiol acidity and disulfide stability similar to those of parent dithiol 2, affirming that hydrophobicity is correlated with catalytic efficacy.

The present data are believed to be the first to indicate that adding a hydrophobic moiety to a small-molecule PDI mimic can have a profound effect on its efficacy as a catalyst. Still, none of the organocatalysts were as efficacious as PDI itself. The molecular mass of PDI (57 kDa) is >$10^2$-fold greater than any of its mimics, enabling optimization of substrate binding and turnover beyond that attainable with small-molecule catalysts. Also, each molecule of PDI has two active sites, and thus provides a higher concentration of dithiol than do the organocatalysts.

Without wishing to be bound by any particular theory, that as with the substrate-binding domains of PDI, the hydrophobicity of dithiols 4-7 likely encourages their interaction with unfolded or misfolded proteins. [60-62, 10, 12, 13, 45, 46] Dithiols having moieties with higher log P values perform better, and aromatic moieties seem to be especially efficacious (FIG. 4B). The increased hydrophobicity of the dithiol ($R_1$ group in formula I) could also increase the rate of the underlying thiol-disulfide interchange chemistry, as hydrophobic (nonpolar environments) are known to lower the free energy of activation for this process. [63]

The log P value of a compound is the logarithm of the compound's partition coefficient between n-octanol and water [$\log(c_{n\text{-}octanol}/c_{water})$]. Log P can be determined experimentally as described for example in Sangster 1989 [59], which is incorporated by reference herein in its entirety for log P values of organic compounds. Log P is a way to assess relative lipophilicity of nonionizable compounds. There are also various ways to calculate log P values. One method calculates log P (Clog P) as a sum of fragment-based contributions and correlations factors. See Mannhold R. et al. [78]

In Table 1, Clog P of $(CH_3)_2N$—$R_1$ is used to provide an estimate of the hydrophobicity (or lipophilicity) of the $R_1$ moieties. For compounds where $R_1$ is —CO—$R_4$, log P is calculated for the corresponding $(CH_3)_2N$—CO—$R_4$ compound as an estimate of the hydrophobicity of the —CO—$R_4$ group.

In Table 1, log P of the dithiols having $R_1$ moieties, the corresponding dimethyl amino-$R_1$ compounds of which, have log P values> about 0 seem to be especially efficacious (Table 1). In specific embodiments, the $R_1$ moieties that are more preferred are those, the corresponding dimethyl amino-$R_1$ compounds of which, have log P values >about 1. For log P values, which may be experimental or calculated, the term about means±10% of the value given (about 1 means 1±10%).

Proteins are linear polymers composed of amino acid monomers. The chemical content of a protein is specified by the order of amino acids that make up the polymer, referred to as its primary structure. The function of a protein is dependent, in addition to the primary structure, on what is referred to as tertiary structure. Tertiary structure refers to the three-dimensional shape into which the protein is bent and fixed as part of the protein expression mechanism in the cells of its host organisms. A critical component in determining the tertiary structure of many proteins is the formation of one or more disulfide bonds between any cysteine residues present in the protein. The disulfide bonds between cysteine residues constrain the protein to certain three dimensional shapes, or tertiary structures. The formation of proper tertiary structure for biological activity takes place naturally in eukaryotic cells during the protein expression and processing system which takes place in the endoplasmic reticulum of eukaryotic cells.

It has become a common procedure of modern biotechnology to produce proteins in heterologous hosts, i. e., organisms which do not normally produce the desired protein. For example, it can be most cost-effective when producing human and mammalian proteins of potential therapeutic or industrial utility, to produce those proteins in prokaryotic organisms, such as the common bacteria *Escherichia coli*. One of the major problems in the use of a prokaryotic host to express a mammalian protein, or any protein from a eukaryotic organism, is the problem of proper tertiary structure of the expressed protein. Because the protein expression and assembly process is much different in heterologous hosts, such prokaryotic hosts do not always form correct disulfide bonds during the process of protein formation. The result is that heterologous mammalian proteins produced in prokaryotic hosts are often recovered from the hosts in a variety of different tertiary structures, only some portion of which will have the desired biological activity. This results in an inefficiency in the protein production system, as well as adding a purification problem since the proteins having the proper tertiary structure and biological activity often must be separated from those which are improperly folded. The process of eukaryotic protein folding, which occurs in the endoplasmic reticulum of eukaryotic cells, is only partially understood. It is known that eukaryotic cells possess an enzyme called protein disulfide isomerase (PDI), a large 57 kilodalton enzyme which helps to ensure that disulfide bonds necessary for biological activity of proteins are formed correctly. One or more forms of PDI are found in the endoplasmic reticulae of all eukaryotic organisms.

Because the proper folding of proteins is of significant scientific and commercial interest, systems have been designed to help to study protein folding. One such system is based on a yeast cells which lack a nuclear gene for the PDI enzyme, and are therefore incapable of catalyzing the formation of the proper disulfide bonds required for biological activity of proteins. Such yeast cells can be grown so long as they harbor a plasmid that produces PDI, but the cells promptly die when the plasmid PDI is removed. The ability of mutant, altered, or engineered forms of PDI to rescue the PDI-deficient yeast cultures from death is a test of the suitability of such altered isoforms to properly fold proteins. Investigation into the function of PDI, and its use in the unscrambling of non-native disulfide bonds, is described by Laboissiere et al. [7] Based on this test system, it has been possible to determine that the motif for PDI activity consists of a particular amino acid domain. This domain is shared in common with the reducing bacterial enzyme thioredoxin. The domain has the consensus sequence CysX-X-Cys, where X is any amino acid. [17]

Compounds of formula I are catalysts of disulfide bond formation. Disulfide bond formation may occur within a protein or polypeptide or between two proteins or polypeptides. Herein the term polypeptide refers to peptides ranging in numbers of amino acid monomers from about 10 to about 50. The term protein is used herein to apply to polypeptides having more than 50 amino acids. The compounds of formula I of this invention can be used to catalyze disulfide bond formation between two cysteines within a polypeptide or protein, or can be used to form one or more disulfide bonds between separate polypeptides and/or proteins, each of which contain at least one cysteine.

Compounds of formula I are catalysts for the isomerization of disulfide bonds and thus can catalyze the disruption (cleavage) of an existing disulfide bond to form a different disulfide bond. Isomerization of disulfide bonds within a polypeptide or protein is illustrated in FIG. 1. The process of isomerization can facilitate the transformation of a polypeptide or proteins having non-native disulfide bonds into a polypeptide or protein having native disulfide bonds. The presence of native disulfide bonds typically being associated with the native biological activity of the polypeptide or protein. In this regard, the compounds of formula I of this invention can be employed to increase the proportion of the native or biologically active form of a polypeptide or protein in a sample of such polypeptides and/or proteins having non-native disulfide bonds.

While it may most often be the goal to increase the amount of polypeptides or proteins having native disulfide bonds, it may also be useful, for example in the study of protein folding or activity, to generate polypeptides or proteins with non-native disulfide bonds. Compounds of formula I can be use, for example, as research reagents, typically in aqueous buffer solutions of selected pH generally for the isomerization of existing disulfide bonds and/or for the formation of non-native or native disulfide bonds.

Preferred compounds of formula I exhibit some minimal level of water solubility. For example, one or more compounds of the invention can be added to solid or liquid growth media of organisms (heterologous hosts) in which a desired protein is to be expressed. In specific embodiments, the concentration of the compound of formula I in the liquid or solid culture medium ranges from 1 microM to up to 10 mM, more typically in liquid culture from 10 microM to 1 mM. It will be appreciated that the concentration in the growth medium must not significantly inhibit growth of the organism and expression of the desired protein. In specific embodiments, a preferred compound of formula I has a minimal solubility of 1 microM in water. In other specific embodiments, a compound of formula I has a minimal solubility of 10 microM in water. In other specific embodiments, a compound of formula I has a minimal solubility of 100 microM in water.

Compounds of formula I can be used for example as a component of a protein refolding (or folding) buffer for carrying out formation or isomerization of internal (intra-chain) disulfide bonds within a polypeptide or protein or for carrying out formation or isomerization of external disulfide bonds formed between different proteins and/or polypeptides (inter-chain disulfide bonds). In specific embodiments, such buffers have pH ranging from 6-12 and more specifically from 7-9 or from 8-9. Such folding buffers can also include a redox buffer that keeps the reduction potential constant at a value that allows disulfide-bond formation. One useful redox buffer is a glutathione-based buffer comprising selected relative amounts of reduced glutathione and oxidized glutathione. In specific embodiments, useful redox buffers include those in which the molar ratio of reduced glutathione (GSH) to oxidized glutathione (GSSG) is 1:10 to 10:1, more preferably 1:1 to 5:1. In a specific embodiment, a useful redox buffer includes those in which the molar ratio of reduced glutathione of oxidized glutathione is 1:1 to 3:1, or more preferably 2:1. In such buffers the concentration of GSH can range from 0.1 to 10 mM or more specifically from 0.5 to 10 mM or more specifically from 1 to 5 mM or more specifically from 0.5 to 2 mM. In specific embodiments, glutathione buffers have concentration of GSH of 0.5 to 2 mM and the ratio of reduced glutathione to oxidized glutathione ranges from 1:1 to 3:1.

In specific embodiments, the invention provides one or more compounds of formula I of the invention in a glutathione buffer. In specific embodiments, the invention provides 1 microM to 10 mM of one or more compounds of formula I of the invention in a glutathione buffer. In specific embodiments, glutathione buffers have concentration of GSH of 0.5 to 2 mM and the ratio of reduced glutathione to oxidized glutathione ranges from 1:1 to 3:1.

Refolding buffers optionally include one or more surface active compounds, e.g., EDTA or detergent, such as dodecyl maltoside, Chaps, SDS, N-lauroylsarcosine (Sarkosyl), polyethylene glycol, octaethylene glycol monolauryl, phospholipidTween 80, or NDSB 201, among others; a chaotropic agent to facilitate unfolding, which preferably is reversible unfolding; an osmolyte, such as a polyol or sugar, which affects osmolality of the buffer; alkali metal, and alkaline earth or ammonium salts. Refolding buffers are predominantly (more than 50% by volume) aqueous, but may contain one or more non-aqueous solvent to facilitate protein/polypeptide solubility, non-aqueous solvents include alcohols, particularly those which are miscible with water, and polar aprotic solvents, such as DMSO or DMF, among others. Non-aqueous solvent can optionally be added to the refolding buffer in the amount of 1%-30% by volume. Chaotropic agents are known in the art and include guanidine hydrochloride, urea, alkali metal hydroxide and combinations thereof. Additional components potentially useful, in combination with a compound of formula I of this invention, for protein refolding are known in the art. See references 74-77 which are each incorporated by reference herein in its entirety for description of such possible components of refolding buffers. See also references 80-82 for additional possible components for refolding buffers, such as sulphobetaines, zwitterionic low molecular weight agents, chaotropic agents (e.g., guanidinium hydrochloride or urea), denaturants, and/or detergents.

The concentration of the compound of formula I in the refolding buffer will typically range from 1 microM to 10 mM in the folding buffer. The concentration used will depend upon the protein/polypeptide and other components in the buffer. The maximum concentration of a given compound of formula I, which exhibits low water solubility, may be enhanced in a given buffer by addition of one or more non-aqueous solvents as discussed above.

Folding and refolding processes are typically carried out until a desired or maximal level of biological activity of the protein or polypeptide is achieved. Protein/polypeptide activity can be followed as a function of time to determine when such maximal activity is achieved for a given refolding buffer.

Methods are known in the art for screening the effectiveness of a given refolding buffer for a given protein/polypeptide or class of such proteins/polypeptides. See Willis et al. 2005 [31] which is incorporated by reference herein in its entirety for such screening methods and for description of components of refolding buffers. Such screens can be employed to determine what components and combinations of components in addition to the compound of formula I are usefully added to such buffers for folding of a given protein/polypeptide. It will be appreciated by one of ordinary skill in the art that kits for performing such screens are commercially available in the art (see, for example, Pierce Protein Refolding Kit, ThermoScientific). Such kits can include DTT, which can be replaced with a compound of formula I of the present invention.

TABLE 1

Properties of PDI and mimics 1-8.

| Catalyst | $pK_a$ | Disulfide $E^{\circ\prime}$ | $logP(R_1CO-N(CH_3)_2)^a$ | Folding yield (%)$^b$ |
|---|---|---|---|---|
| (None) | — | — | — | 45 ± 2 |
| PDI | 6.7$^c$ | −0.180 V | — | 87 ± 2 |
| 1 (BMC) | 8.3; 9.9$^d$ | −0.232 V | — | 42 ± 2 |
| 2 | 8.0; 9.2 | −0.192 V | 0.10 | 50 ± 2 |
| 3 | ND | ND | −0.74 | 45 ± 2 |
| 4 | ND | ND | 0.66 | 54 ± 4 |
| 5 | 8.1; 9.3 | −0.203 V | 1.67 | 57 ± 1 |
| 6 | ND | ND | 0.90 | 60 ± 2 |
| 7 | 8.1; 9.4 | −0.206 V | 1.82 | 66 ± 2 |
| 8 | ND | ND | 2.06 | ND |

$^a$Values were calculated for dimethylamine in dithiol 2 and the tertiary amide moiety in dithiols 3-8 (e.g., N,N-dimethylacetamide for dithiol 3) with software from Molinspiration (Slovenský Grob, Slovak Republic), and are similar to known experimental values. [59]
$^b$Values are for the unscrambling of sRNase A to give native RNase A by 1 mM catalyst, as in FIG. 4.
$^c$Values for the N-terminal cysteine in the active site of PDI. [23]
$^d$Values from ref. [30].
ND, not determined.

Folding and refolding processes employing a compound of formula I of the invention can be carried out in vitro or in vivo.

The production of proteins that contain disulfide bonds by recombinant DNA technology often leads to the aggregation of misfolded proteins. [64, 65] These aggregates must be reduced, denatured, and solubilized to enable proper folding. Approximately 20% of human proteins are predicted to contain disulfide bonds between cysteine residues[66], including many of high pharmaceutical relevance. [67, 68] For example, antibodies contain at least 12 intrachain and 4 interchain disulfide bonds [69], and there are now greater than 3000 distinct antibodies in clinical development [70], including about 30 antibody-drug conjugate. [85] The catalysts of this invention of formula I can be employed, for example, in the production of antibodies and other biologics.

In specific embodiments, the compounds of formula I of the invention are useful for obtaining active proteins or polypeptides by refolding of recombinant proteins or polypeptides of bacterial inclusion bodies. Production of recombinant proteins or polypeptides in bacteria, such as *Escherichia coli* can result in inactive protein aggregated in inclusion bodies. See Vallejo et al. [79] for a review of isolation, optional purification and refolding of proteins from inclusion bodies. This reference is incorporated by reference herein for this description. Compounds of formula I herein can be employed in the refolding of proteins or polypeptides isolated from inclusion bodies.

In specific embodiments, the invention provides a method for forming a disulfide bond in a polypepetide or protein containing at least two cysteines which comprises contacting the polypeptide or protein with a catalyst of formula I.

In a specific embodiment, the invention provides a method for isomerizing disulfide bonds in a polypeptide or protein containing at least two disulfide bonds which comprises contacting the polypeptide or protein with a catalyst of formula I.

Compounds of formula I are prepared as described in the examples. The methods described herein, in view of what is generally well known in the art, can be used or routinely adapted to prepare compounds of formula I. In particular, protected dicarboxylate 12, illustrated below having generic protecting groups (Pr) can be reacted with $R_1$—COCl to acylate the central nitrogen.

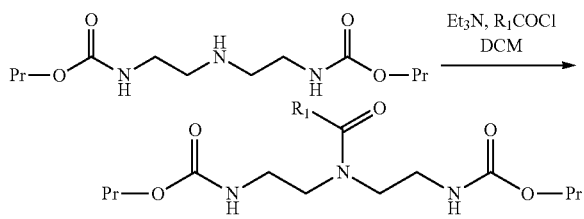

The resulting protected and acylated dicarboxylate is then converted to the corresponding dithiol, as illustrated in the Examples. PrO—CO— groups are protecting groups suitable for protecting the amine during the coupling reaction of the carbonyl chloride to the central nitrogen, such protecting groups are well known in the art. In a specific embodiment, the Pr group is an alkyl group having 1-6 carbon atoms, including a methyl or t-butyl, or a benzyl group.

Thus, compounds of formula II are useful at least in the preparation of the compounds of formula I of this invention:

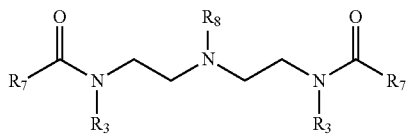

where:
each $R_3$ is independently hydrogen or an alkyl having 1-3 carbon atoms;
$R_8$ is hydrogen, —CO—$R_1$ where $R_1$ is as defined for formula I above or —CO—O—Pr; and
$R_7$ is X—CH$_2$—, where X is a chlorine or bromine; HS—CH$_2$—; $R_9$—CO—S—CH$_2$—, where $R_9$ is an alkyl group having 1-3 carbon atoms; or Pr—O—, where Pr—O—CO— is an amine protecting group and Pr is an alkyl group having 1-6 carbon atoms, including a methyl group or a t-butyl group, or a benzyl group.

In specific embodiments of formula II, the variables are selected to exclude compounds of formula I. Specifically, when $R_8$ is —CO—$R_1$, then $R_7$ is a group other than RCO—S—CH$_2$— or HSCH$_2$—.

In a specific embodiment, not all of $R_3$ and $R_8$ are hydrogens, where other varibles are as defined above.

In a specific embodiment, neither $R_3$ is hydrogen and other variables are as defined above.

In a specific embodiment, neither $R_3$ nor $R_8$ is a hydrogen and other variables are as defined above.

Formula II specifically includes compounds where $R_8$ is —CO—$R_1$ and both $R_7$ are X—CH$_2$—, where X is a chlorine or bromine; or both $R_7$ are Pr—O— as defined above. More specifically, formula II includes compounds where $R_8$ is hydrogen and $R_7$ is X—CH$_2$—, where X is a chlorine or bromine; HS—CH$_2$—; $R_9$—CO—S—CH$_2$—, where $R_9$ is an alkyl group having 1-3 carbon atoms; or Pr—O—, where Pr—O—CO— is an amine protecting group and Pr is an alkyl group having 1-6 carbon atoms, including a methyl group or a t-butyl group, or a benzyl group, particularly where both $R_7$ are the same group. The compounds of formula II specifically include dithiol compound 2 (FIG. 2). However, in a specific embodiment, dithiol 2 can be excluded from the compounds of formula II (when $R_8$ is hydrogen, both $R_7$ are not HS—CH$_2$—).

In a specific embodiment, the dithiol compound 2 is useful as a catalyst for formation of or isomerization of disulfide bonds.

In specific embodiments, each of compounds 2, 3, 4, 5, 6, 7 or 8 is useful as a catalyst for formation of or isomerization of disulfide bonds.

In specific embodiments, each of compounds 32, 33, 34, 35, 36 or 37 is useful as a catalyst for formation of or isomerization of disulfide bonds.

The term aliphatic as used herein refers to compounds or monovalent chemical groups containing only carbon and hydrogen atoms. The monovalent aliphatic group is formally derived by removal of a hydrogen from an aliphatic compound (i.e., a methyl group derives from methane). Aliphatic groups may be linear, branched or cyclic and may contain one or more double or triple bonds. Aliphatic groups do not contain any aromatic rings. Aliphatic groups include alkyl groups, alkenyl groups and alkynyl groups. In a specific embodiment, aliphatic groups have 1-20 carbon atoms. In other embodiments, aliphatic groups have 3-20 carbon atoms. In other embodiments, aliphatic groups have 1-10, 2-10 or 3-10 carbon atoms. In other embodiments, aliphatic groups have 5-12, 5-10 or 5-8 carbon atoms. In other embodiments, aliphatic groups have 1-8, 2-8 or 3-8 carbon atoms. In other embodiments, aliphatic groups have 1-6, 2-6 or 3-6 carbon atoms. Aliphatic groups are optionally substituted as described herein. With respect to the naming of aliphatic groups, the monovalent site of attachment of the group is typically used to name the group a propyl group can be an n-propyl group or an isopropyl group as is known in the art. As is known in the art, in designating substitution or the position of a double or triple bond in an aliphatic groups, the site of substitution or the double bond is typically named with respect to the monovalent site of attachment of the group, e.g. a methylcyclohexyl group can be a 2-, a 3- or a 4-methylcyclohexyl group.

The term alicyclic as used herein refers to compounds or monovalent chemical groups containing only carbon and hydrogen atoms. The group is formally formed by removal of a hydrogen from a ring or non-ring carbon of an alicyclic compound (a cycohexyl group derives formally from cyclohexane). Alicyclic groups have at least one carbon ring which may have no unsaturated bonds or which may have one or more double or triple bonds. Alicyclic rings are not aromatic. Alicyclic groups may contain portions that are non-cyclic, e.g., a cycloalkyl or cycloalkenyl group substituted with linear or branched (but not cyclic) alkyl or alkenyl group. The carbon ring of the alicyclic group can have 3-12 ring atoms. In a specific embodiment, the carbon ring of the alicyclic group can have 3-10, 3-8, 5-10, 5-8 or 5 or 6 ring members. In specific embodiments, the carbon ring having 3-12 ring atoms can have one, two, three or four double bonds dependent upon ring size. In specific embodiments, rings having 5-8 carbon atoms have one or two double bonds. Alicyclic groups herein are optionally substituted as described herein. Alicyclic groups include among other cycloalkyl, cycolalkenyl groups, specifically cyclopropyl, cycopentyl, cyclohexyl, cyclohexenyl, cycloheptyl, cyclooocyl, cyclooctatrienyl, and cyclodecyl, among others. Alicyclic groups include bicyclic and tricyclic alkyl groups, such as bicyclo[2.2.1]heptyl, bicyclo [4.4.0] decanyl, adamantly, and norbornyl. The naming of the site of monovalent attachment of a multicyclic group is typically based on the standard ring numbering system employed in naming alicyclic compounds.

The term aryl is used herein to refer to aromatic compounds or monovalent aromatic groups having at least one phenyl ring. The aryl group is formally formed by removal of a hydrogen from a ring or non-ring carbon of an aromatic (aryl) compound. Aryl groups unless substituted contain only carbon and hydrogen atoms. Aryl groups include those with one or two phenyl rings which may be linked by a single bond or an alkyl linker (e.g., biphenyl) and those in which the phenyl rings are fused (e.g., naphthyl). In specific embodiments, the phenyl ring may be fused or linked to a non-aromatic carbon ring, e.g., indanyl or indenyl. In specific embodiments, aryl groups are those having a portion that is non-aromatic, such a benzyl and phenethyl groups (such groups can be seen as alkyl groups substituted with a phenyl group). In specific embodiments, aryl groups are those substituted with an alkyl or alkenyl group, such as 4-methylphenyl, 2-ethylphenyl, or 4-vinylphenyl. In specific embodiments, aryl groups contain 6-20 carbon atoms, 6-12 carbon atoms or 6-10 carbon atoms. Aryl groups are optionally substituted as described herein. It will be appreciated that a given aryl group may have more than one possible monovalent site for attachment to other chemical species. For example, an unsubstituted naphthyl group may be bonded at the 1 or 2 ring position on the naphthyl ring with attachment site distinguished as indicated in naphtha-1-yl or naphtha-2-yl. When no attachment site is labeled in the name of the group, it is intended that any possible attachment site (all of which would be readily apparent to one of ordinary skill in the art) are included.

An acyl group is an R'—CO— group where R' in general is a hydrogen, an alicyclic group (an alkyl, alkenyl or alkynyl) or an aryl group as described above. In specific embodiments, acyl groups have 1-20, 1-12 or 1-6 carbon atoms and optionally one double bond or one triple bond. Unless otherwise defined, in specific embodiments, R' is an alkyl having 1-8 carbon atoms, an alkenyl having 3-8 or an alkynyl group having 3-8 carbon atoms. Examples of acyl groups include acetyl, benzoyl, propionyl, isobutyryl, or oxalyl. The R' group of acyl groups are optionally substituted as described herein. When R' is hydrogen, the group is a formyl group. An acetyl group is a $CH_3$—CO— group. Another exemplary acyl group is a benzyloxy group.

An alkoxy group is an R'—O— group where R' is an alkyl group as defined above. An alkenoxy group is an R'—O— group where R' is an alkyl group as defined above. In a specific embodiment, the alkenoxy group is a group other than one in which the double bond is alpha to the oxygen.

Groups herein are optionally substituted most generally with one or more alky, alkenyl, alkynyl, aryl, halogens, alkoxy or alkenoxy group. In specific embodiments dependent upon the number of carbons in the group, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substitution is substitution with 1 non-hydrogen substituents. In specific embodiments, optional substituents contain 6 or fewer carbon atoms. In specific embodiments, optional substituents contain 3 or fewer carbon atoms.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

With respect to the various compounds of the invention, the atoms therein may have various isotopic forms, e.g., isotopes of hydrogen include deuterium and tritium. All isotopic variants of compounds of the invention are included within the invention and particularly included at deuterium and 13C isotopic variants. It will be appreciated that such isotopic variants may be useful for carrying out various chemical and biological analyses, investigations of reaction mechanisms and the like. Methods for making isotopic variants are known in the art.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are to be understood to be disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Materials and Methods

Commercial reagents were used without further purification. β-Mercaptoethanol (βME), oxidized β-mercaptoethanol (βME$^{ox}$), and diethylenetriamine were from Sigma-Aldrich (St. Louis, Mo.). RNase A was from Sigma-Aldrich and purified further by cation-exchange chromatography. The RNase A substrate 6-FAM-dArUdAdA-6-TAMRA was from Integrated DNA Technologies (Coralville, Iowa). All glassware was oven- or flame-dried, and reactions were performed under $N_2$(g) unless stated otherwise. Dichloromethane and tetrahydrofuran (THF) were dried over a column of alumina. Triethylamine was dried over a column of alumina and purified further by passage through an isocyanate scrubbing column. Flash chromatography was performed with columns of 40-63 Å silica, 230-400 mesh from Silicycle (Québec City, Canada). Thin-layer chromatography (TLC) was performed on plates of EMD 250-μm silica 60-F$_{254}$. The term "concentrated under reduced pressure" refers to the removal of solvents and other volatile materials using a rotary evaporator at water aspirator pressure (<20 torr) while maintaining the water-bath temperature below 40° C. Residual solvent was removed from samples at high vacuum (<0.1 torr). The term "high vacuum" refers to vacuum achieved by a mechanical belt-drive oil pump. Analytical samples of all protein folding catalysts were obtained with a preparative HPLC instrument from Shimadzu (Kyoto, Japan), which was equipped with a C18 reverse-phase preparative column, a Prominence diode array detector, and fraction collector. Equilibrium and reduction potential assays were performed using an analytical HPLC instrument from Waters (Milford, Mass.), which was equipped with a Waters 996 photodiode array detector, Empower 2 software, and a Varian C18 reverse-phase column. Thiol p$K_a$ values were determined with a Varian Cary 60 UV-Vis spectrophotometer. Fluorescence was measured with an Infinite M1000 plate reader from Tecan (Männedorf, Switzerland). Calculations and rate constants were performed with Prism 6 software from GraphPad (La Jolla, Calif.). All NMR spectra were acquired at ambient temperature with a Bruker DMX-400 Avance spectrometer and Bruker III 500ii with cryoprobe spectrometer at the National Magnetic Resonance Facility at Madison (NMRFAM), and were referenced to TMS or residual solvent.

Example 2

Chemical Synthesis

A.

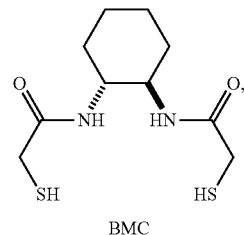

BMC (1) was synthesized as a racemate from (±)-trans-1,2-diaminocyclohexane as described previously. [9] An analytically pure sample of BMC was obtained by reverse-phase HPLC using a preparatory C18 column and a linear gradient of 10-80% v/v acetonitrile (0.1% v/v TFA) in water (0.1% v/v TFA) over 45 min. BMC eluted at 23 min and, after lyophilization, was isolated as a white powder.

$^1$H NMR (400 MHz, DMSO-d$_6$) δ=7.83 (d, J=5.3 Hz, 2H), 3.52-3.48 (m, 2H), 3.09-2.99 (m, 4H), 2.60 (t, J=7.9 Hz, 2H), 1.79-1.77 (m, 2H), 1.66-1.65 (m, 2H), 1.24-1.20 (m, 4H); $^{13}$C NMR (100 MHz, CDCl$_3$) δ=169.2, 52.2, 31.7, 27.3, 24.3; HRMS (ESI) calculated for [C$_{10}$H$_{19}$N$_2$O$_2$S$_2$]$^+$ (M+H$^+$) requires m/z=263.0883. found 263.0895.

B.

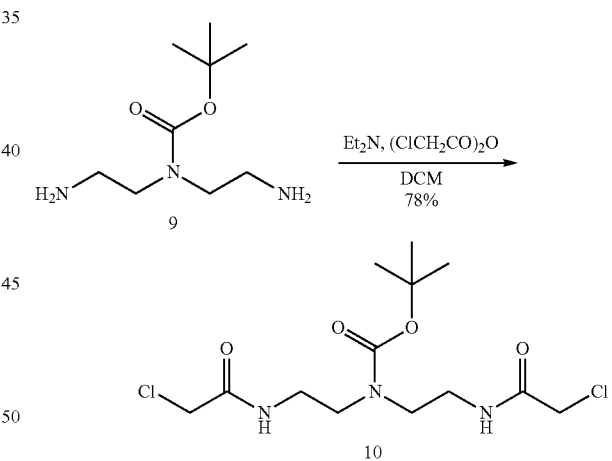

To a flame-dried round-bottom flask was added 9 (0.847 g, 4.166 mmol), which was synthesized as described previously. [30] Dichloromethane (50 mL) was then added, and the resulting solution was cooled to 0° C. under an atmosphere of N$_2$(g). Next, triethylamine (2.3 mL, 16.667 mmol) and chloro acetic anhydride (1.567 g, 9.167 mmol) were added, and the reaction mixture was stirred for 30 min before being quenched by the addition of 50 mL of saturated NaHCO$_3$(aq). The organic layer was extracted and washed with water (2×25 mL). The organic extract was then dried over MgSO$_4$(s), filtered, and concentrated under reduced pressure, and the product was purified by column chromatography (silica, EtOAc) yielding 10 as a colorless oil (1.154 g, 78%).

$^1$H NMR (400 MHz, CDCl$_3$) δ=7.36 (br, s, 1H), 6.99 (br, s, 1H), 4.09-3.98 (m, 4H), 3.48-3.38 (m, 8H), 1.49 (s, 9H); $^{13}$C NMR (100 MHz, CDCl$_3$) δ=166.9, 166.4, 156.6, 81.0, 47.1, 46.1, 42.5, 39.8, 38.8, 28.3; HRMS (ESI) calculated for [C$_{13}$H$_{23}$O$_2$N$_3$O$_4$Na]$^+$ (M+Na$^+$) requires m/z=378.0958. found 378.0938.

C.

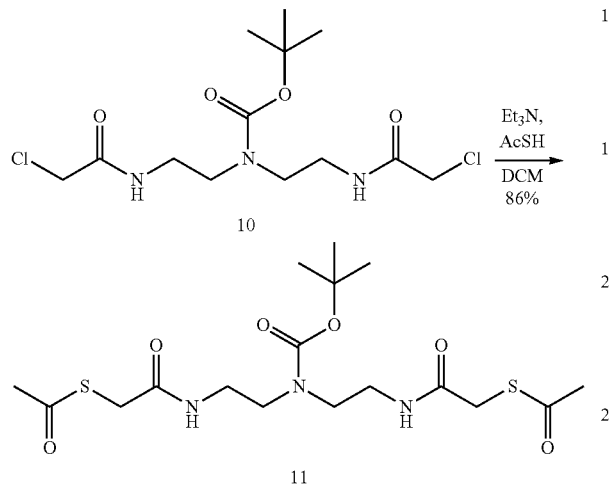

Compound 10 (1.154 g, 3.239 mmol) was placed in a round-bottom flask and dissolved in 30 mL of dichloromethane, and the resulting solutions was placed under an atmosphere of N$_2$(g). Triethylamine (2.3 mL, 16.208 mmol) and thioacetic acid (0.5 mL, 7.131 mmol) were then added, and the resulting solution was stirred under N$_2$(g). After 16 h, the reaction mixture was concentrated, and the product was purified by column chromatography (silica, EtOAc), giving 11 as a colorless oil (2.792 g, 86%).

$^1$H NMR (400 MHz, CDCl$_3$) δ=6.81 (br, s, 2H), 3.56 (s, 4H), 3.42-3.29 (m, 8H), 2.41 (s, 6H), 1.49 (s, 9H); $^{13}$C NMR (100 MHz, CDCl$_3$) δ=195.1, 194.7, 168.2, 156.3, 80.3, 47.9, 47.1, 39.7, 38.9, 32.9, 30.1, 28.3; HRMS (ESI) calculated for [C$_{17}$H$_{29}$N$_3$O$_6$S$_2$Na]$^+$ (M+Na$^+$) requires m/z=458.1390. found 458.1405.

D.

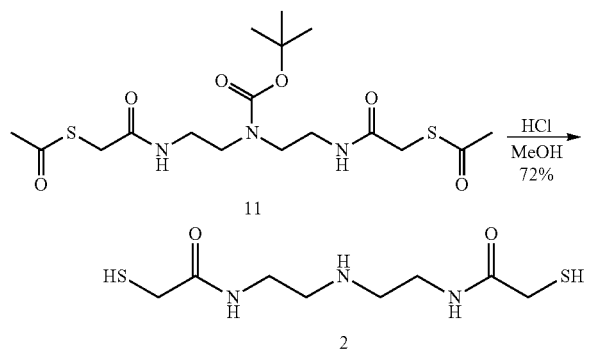

A flame-dried round-bottom flask was charged with compound 11 (0.178 g, 0.409 mmol) and placed under an atmosphere of N$_2$(g). Anhydrous methanol (4 mL) followed by 2 mL of 3 N HCl in methanol were then added, and the reaction mixture was stirred under N$_2$(g). Upon confirmation by TLC that the Boc group had been removed, the reaction mixture was concentrated under reduced pressure, and the product was purified by reverse-phase HPLC using a preparatory C18 column and a linear gradient of 10-50% v/v acetonitrile (0.1% v/v TFA) in water (0.1% v/v TFA) over 55 min. Dithiol 2 eluted as its TFA salt at 12.5 min and, after lyophilization, was isolated as a white solid (0.108 g, 72%).

$^1$H NMR (400 MHz, DMSO-d$_6$) δ=8.76 (br, s, 2H), 8.33 (br, s, 2H), 3.5203.35 (m, 8H), 3.15 (d, J=7.7 Hz, 4H), 2.88 (t, J=7.7 Hz, 2H); $^{13}$C NMR (100 MHz, DMSO-d$_6$) δ=170.4, 46.1, 35.5, 27.2; HRMS (ESI) calculated for [C$_8$H$_{18}$N$_3$O$_2$S$_2$]$^+$ (M+H$^+$) requires m/z=252.0835. found 252.0839.

E.

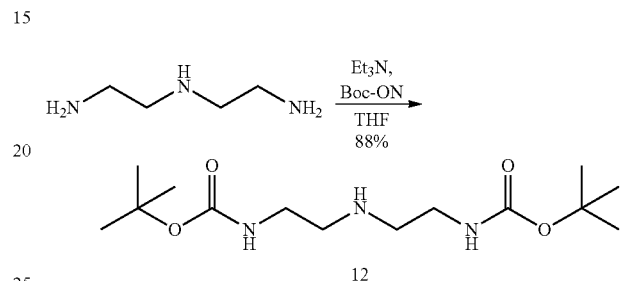

Synthesis of compound 12 was accomplished by closely following a procedure reported previously. [71] Specifically, diethylenetriamine (2.003 g, 19.415 mmol) and triethylamine (8.1 mL, 58.245 mmol) were dissolved in 100 mL of THF, and the resulting solutions was cooled to 0° C. in an ice bath and placed under an atmosphere of N$_2$(g). Next, a solution of 2-(boc-oxyimino)-2-phenylacetonitrile (Boc-ON) (9.563 g, 38.832 mmol) in 40 mL of THF was added dropwise. The reaction mixture was stirred for 1 h on ice and then for another 1 h at room temperature. The solvent was removed under reduced pressure, and the residue was dissolved in 200 mL of dichloromethane and washed with 5% w/v NaOH. The organic extract was then dried with MgSO$_4$ (s), filtered, concentrated under reduced pressure, and the product was purified by column chromatography (silica, 10% v/v methanol in dichloromethane, 1% ammonium hydroxide), yielding 12 as a colorless oil (5.184 g, 88%).

$^1$H NMR (400 MHz, CDCl$_3$) δ=4.95 (br, s, 2H), 3.22 (q, J=5.9 Hz, 4H), 2.73 (t, J=5.9 Hz, 4H), 1.45 (s, 18H); $^{13}$C NMR (100 MHz, CDCl$_3$) δ=156.3, 79.4, 49.0, 40.5, 28.6; HRMS (ESI) calculated for [C$_{14}$H$_{30}$N$_3$O$_4$]$^+$ (M+H$^+$) requires m/z=304.2231. found 304.2230.

F.

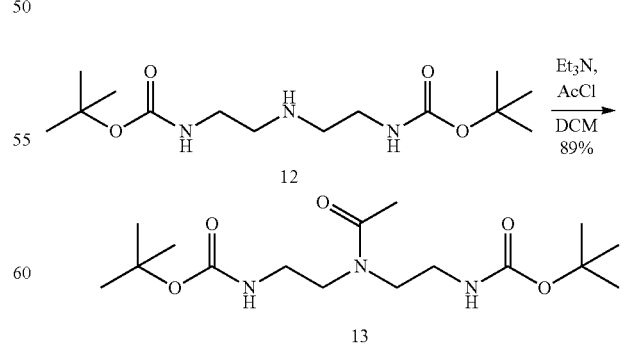

Compound 12 (0.419 g, 1.381 mmol) was placed in a flame-dried round-bottom flask, dissolved in 15 mL of anhydrous dichloromethane, and cooled to 0° C. in an ice bath under an inert atmosphere. Triethylamine (0.72 mL, 5.17 mmol) and acetyl chloride (0.16 mL, 2.29 mmol) were then added, and the resulting solution was stirred at 0° C. for 1 h and at room temperature for another 2 h. The reaction mixture was then concentrated under reduced pressure, and the product was purified by column chromatography (silica, EtOAc), yielding 13 as a colorless oil (0.425 g, 89%).

$^1$H NMR (400 MHz, CDCl$_3$) δ=5.20 (br, s, 1H), 5.11 (br, s, 1H), 3.47-3.43 (m, 4H), 3.32-3.25 (m, 4H), 2.12 (s, 3H), 1.43 (s, 18H); $^{13}$C NMR (100 MHz, CDCl$_3$) δ=172.2, 156.6, 156.2, 79.8, 79.5, 49.4, 45.8, 39.7, 39.3, 28.6, 28.5, 21.6; HRMS (ESI) calculated for [C$_{16}$H$_{32}$N$_3$O$_5$]$^+$ (M+H$^+$) requires m/z=346.2337. found 346.2338.

G.

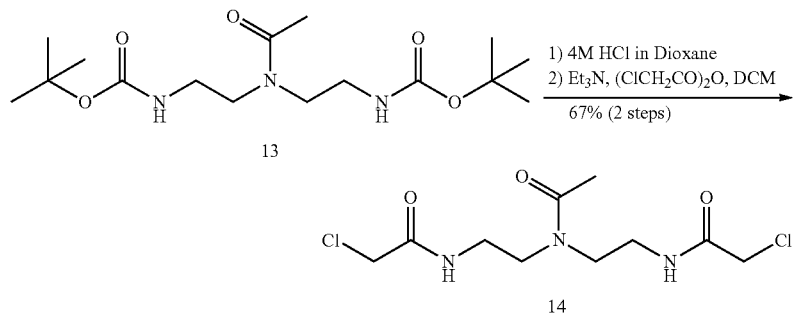

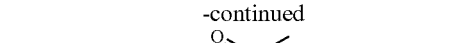

A round-bottom flask was charged with 14 (0.246 g, 0.824 mmol) dissolved in 15 mL of dichloromethane, and placed under an atmosphere of N$_2$(g). Triethylamine (0.57 mL, 4.12 mmol) and thioacetic acid (0.13 mL, 1.81 mmol) were then added, and the reaction mixture was stirred under N$_2$(g). After 16 h, the mixture was concentrated under reduced pressure, and the product was purified by column chromatography (silica, 10% v/v methanol in dichloromethane), providing 15 as a yellow oil (0.286 g, 92%).

HCl (40 mL, 4M) in dioxane was added to a round-bottom flask containing 13 (0.425 g, 1.230 mmol). The resulting solution was stirred overnight and then concentrated under reduced pressure. The product was then partially dissolved in 20 mL of dichloromethane, and the resulting slurry was cooled to 0° C. in an ice bath and placed under an atmosphere of N$_2$(g). Triethylamine (1.1 mL, 7.9 mmol) and chloroacetic anhydride (0.463 g, 2.706 mmol) were then added, and the reaction mixture was stirred for 30 min before being quenched by the addition of 50 mL of saturated NaHCO$_3$(aq). The organic layer was extracted and washed with water (2×25 mL). The organic extract was then dried with MgSO$_4$(s), filtered, and concentrated under reduced pressure, and the product was purified by column chromatography (silica, 10% v/v methanol in dichloromethane), yielding 14 as a colorless oil (0.245 g, 67%).

$^1$H NMR (400 MHz, CDCl$_3$) δ=7.33 (br, s, 1H), 7.06 (br, s, 1H), 4.06 (s, 2H), 4.02 (s, 2H), 3.60-3.56 (m, 2H), 3.52-3.47 (m, 6H), 2.15 (s, 3H); $^{13}$C NMR (100 MHz, CDCl$_3$) δ=172.5, 167.2, 166.9, 48.7, 45.4, 42.6, 39.6, 38.8, 21.5; HRMS (ESI) calculated for [C$_{10}$H$_{18}$Cl$_2$N$_3$O$_3$]$^+$ (M+H$^+$) requires m/z=298.0713. found 298.0720.

H.

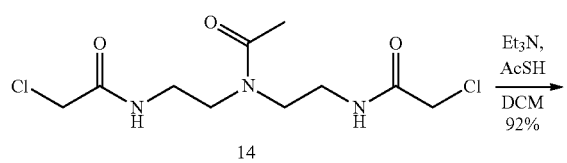

$^1$H NMR (400 MHz, CDCl$_3$) δ=6.91 (br, s, 2H), 3.58 (s, 2H), 3.54 (s, 2H), 3.52-3.35 (m, 8H), 2.44 (s, 3H), 2.41 (s, 3H), 2.09 (s, 3H); $^{13}$C NMR (100 MHz, CDCl$_3$) δ=195.8, 195.2, 172.6, 168.9, 168.7, 48.8, 45.1, 39.4, 38.9, 33.1, 33.0, 30.5, 30.4, 21.6; HRMS (ESI) calculated for [C$_{14}$H$_{24}$N$_3$O$_5$S$_2$]$^+$ (M+H$^+$) requires m/z=378.1152. found 378.1150.

I.

A flame-dried round-bottom flask was charged with 15 (0.159 g, 0.421 mmol) and placed under an atmosphere of N$_2$(g). Anhydrous methanol (4 mL) followed by 2 mL of 3 N HCl in methanol were then added, and the resulting solution was stirred under N$_2$(g). After 16 h, the reaction mixture was concentrated under reduced pressure, and the product was purified by reverse-phase HPLC using a preparatory C18 column and a linear gradient of 10-80% v/v acetonitrile (0.1% v/v TFA) in water (0.1% v/v TFA) over 45 min. Dithiol 3 eluted at 17 min and, after lyophilization, was isolated as a colorless oil (95.11 mg, 77%).

$^1$H NMR (400 MHz, DMSO-d$_6$) δ=8.19 (t, J=6.0 Hz, 1H), 8.07 (t, J=5.9 Hz, 1H), 3.33-3.26 (m, 4H), 3.24-3.16 (m, 4H), 3.11 (d, J=8.6 Hz, 2H), 3.06 (d, J=8.6 Hz, 2H), 2.74 (t, J=8.6 Hz, 1H), 2.71 (t, J=8.6 Hz, 1H), 1.99 (s, 3H); $^{13}$C NMR (100 MHz, DMSO-d$_6$) δ=170.1, 170.0, 169.9, 47.8, 44.65, 37.7, 36.9, 27.1, 27.0, 21.3; HRMS (ESI) calculated for [C$_{10}$H$_{20}$N$_3$O$_3$S$_2$]$^+$ (M+H$^+$) requires m/z=294.0942. found 294.0941.

J.

HCl (50 mL, 4M) in dioxane was added to a round-bottom flask containing 16 (0.625 g, 1.673 mmol). The reaction mixture was left to stir overnight and then concentrated under reduced pressure. The compound was then partially dissolved in 20 mL of dichloromethane, cooled to 0° C. in an ice bath, and placed under an atmosphere of N$_2$(g). Triethylamine (1.2 mL, 8.4 mmol) and chloroacetic anhydride (0.629 g, 3.681 mmol) were then added, and the

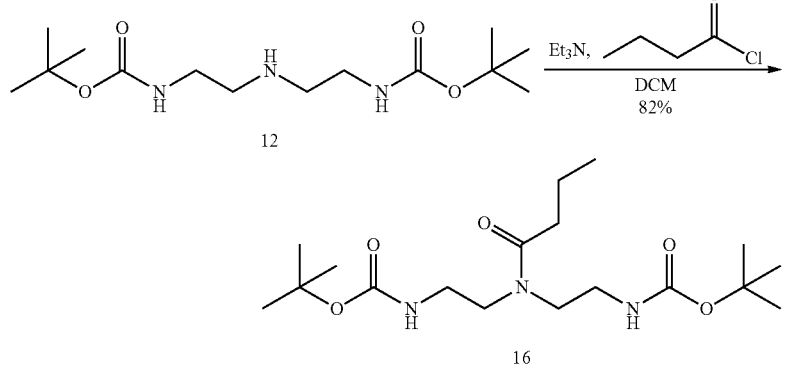

Compound 12 (0.619 g, 2.040 mmol) was placed in a flame-dried round-bottom flask and dissolved in 20 mL of anhydrous dichloromethane, and the resulting solution was cooled to 0° C. in an ice bath under an atmosphere of N$_2$(g). Triethylamine (1.4 mL, 10.2 mmol) and butyryl chloride (0.25 mL, 2.45 mmol) were then added, and the reaction mixture was stirred at 0° C. for 1 h and at room temperature for another 2 h. The reaction mixture was then concentrated under reduced pressure, and the product was purified by column chromatography (silica, EtOAc) yielding 16 as a colorless oil (0.625 g, 82%).

$^1$H NMR (400 MHz, CDCl$_3$) δ=5.39 (br, s, 1H), 5.30 (br, s, 1H), 3.48-3.42 (m, 4H), 3.32-3.25 (m, 4H), 2.32 (t, J=7.5 Hz, 2H), 1.65 (sex, J=7.5 Hz, 2H), 1.43 (s, 9H), 1.42 (s, 9H), 0.95 (t, J=7.5 Hz, 3H); $^{13}$C NMR (100 MHz, CDCl$_3$) δ=174.7, 156.6, 156.1, 79.6, 79.3, 48.4, 45.7, 39.6, 39.3, 34.9, 28.4, 18.8, 13.9; HRMS (ESI) calculated for [C$_{18}$H$_{36}$N$_3$O$_5$]$^+$ (M+H$^+$) requires m/z=374.2650. found 374.2655.

K reaction mixture was stirred for 30 min before being quenched by the addition of 50 mL of saturated NaHCO$_3$ (aq). The organic layer was extracted and washed twice with 25 mL of water. The organic extract was then dried with anhydrous MgSO$_4$(s), filtered, and concentrated under reduced pressure, and the product was purified by column chromatography (silica, 10% v/v methanol in dichloromethane), yielding 17 as a colorless oil (0.377 g, 69%).

$^1$H NMR (400 MHz, CDCl$_3$) δ=7.48 (br, s, 1H), 7.26 (br, s, 1H), 4.06 (s, 2H), 4.00 (s, 2H), 3.58 (t, J=6.1 Hz, 2H), 3.52-3.46 (m, 6H), 2.34 (t, J=7.4 Hz, 2H), 1.66 (sex, J=7.4 Hz, 2H), 0.96 (t, J=7.4 Hz, 3H); $^{13}$C NMR (100 MHz, CDCl$_3$) δ=175.0, 167.1, 166.9, 47.6, 45.2, 42.5, 39.5, 38.7, 34.9, 18.9, 14.0; HRMS (ESI) calculated for [C$_{12}$H$_{22}$O$_2$N$_3$O$_3$]$^+$ (M+H$^+$) requires m/z=326.1033. found 326.1036.

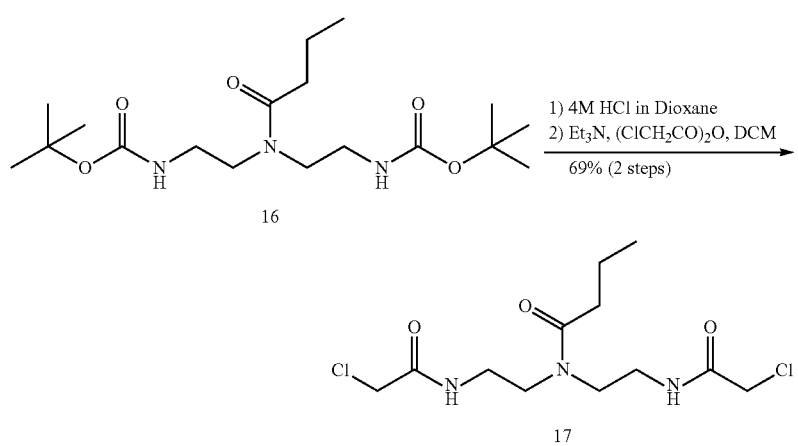

L.

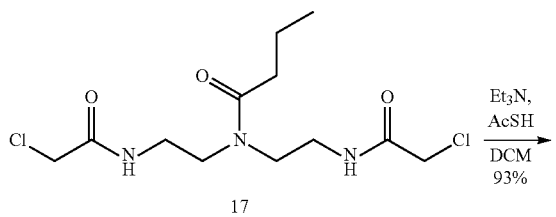

A round-bottom flask was charged with 17 (0.377 g, 1.154 mmol) dissolved in 20 mL of dichloromethane, and placed under an atmosphere of $N_2(g)$. Triethylamine (0.80 mL, 5.77 mmol) and thioacetic acid (0.18 mL, 2.54 mmol) were then added, and the resulting solution was stirred under $N_2(g)$. After 16 h, the reaction mixture was concentrated under reduced pressure, and the product was purified by column chromatography (silica, 10% v/v methanol in dichloromethane), providing 18 as a yellow oil (0.435 g, 93%).

$^1$H NMR (400 MHz, CDCl$_3$) δ=7.13 (br, s, 2H), 3.59 (s, 2H), 3.56 (s, 2H), 3.51-3.37 (m, 8H), 2.42 (s, 3H), 2.41 (s, 3H), 2.32 (t, J=7.5 Hz, 2H), 1.64 (sex, J=7.5 Hz, 2H), 0.96 (t, J=7.5 Hz, 3H); $^{13}$C NMR (100 MHz, CDCl$_3$) δ=195.6, 195.0, 174.9, 168.8, 168.6, 47.6, 45.1, 39.4, 38.8, 34.9, 33.0, 30.3, 30.2, 18.8, 13.9; HRMS (ESI) calculated for [C$_{16}$H$_{28}$N$_3$O$_5$S$_2$]$^+$ (M+Na$^+$) requires m/z=406.1465. found 406.1459.

M.

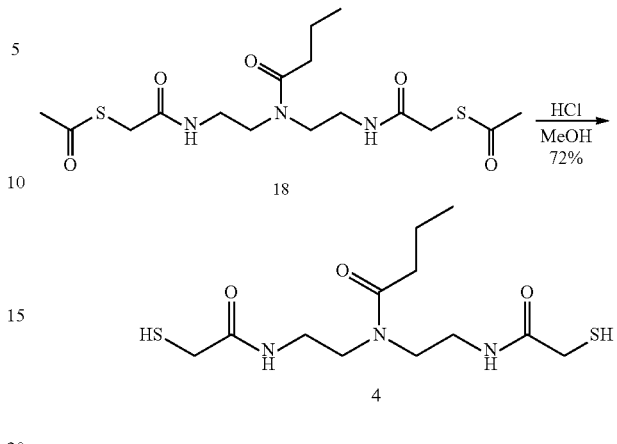

A flame-dried round-bottom flask was charged with 18 (0.111 g, 0.274 mmol) and placed under an atmosphere of $N_2(g)$. Anhydrous methanol (6 mL) followed by 3 mL of 3 N HCl in methanol was then added, and the resulting solution was stirred under $N_2(g)$. After 16 h, the reaction mixture was concentrated under reduced pressure, and the product was purified by reverse-phase HPLC using a preparatory C18 column and a linear gradient of 10-80% v/v acetonitrile (0.1% v/v TFA) in water (0.1% v/v TFA) over 45 min. Dithiol 4 eluted at 22 min and, after lyophilization, was isolated as a colorless oil (63.42 mg, 72%).

$^1$H NMR (400 MHz, DMSO-d$_6$) δ=8.19 (t, J=Hz, 1H), 8.05 (t, J=Hz, 1H), 3.34-3.28 (m, 4H), 3.23-3.15 (m, 4H), 3.09 (d, J=8.0 Hz, 2H), 3.06 (d, J=8.0 Hz, 2H), 2.74 (t, J=8.0 Hz, 1H), 2.71 (t, J=8.0 Hz, 1H), 2.27 (t, J=7.4 Hz, 2H), 1.51 (sex, J=7.4 Hz, 2H), 0.87 (t, J=7.4 Hz, 3H); $^{13}$C NMR (100 MHz, DMSO-d$_6$) δ=172.3, 170.0, 169.7, 46.8, 45.0, 37.8, 37.0, 34.0, 27.1, 27.0, 18.3, 13.8; HRMS (ESI) calculated for [C$_{12}$H$_{24}$N$_3$O$_3$S$_2$]$^+$ (M+Na$^+$) requires m/z=322.1254. found 322.1258.

N.

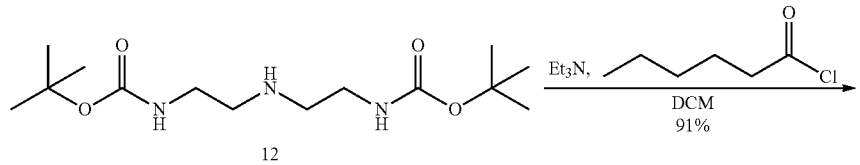

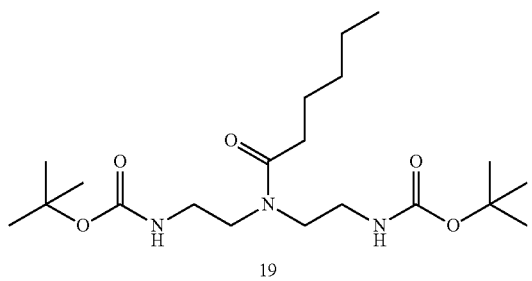

Compound 12 (1.534 g, 5.056 mmol) was placed in a flame-dried round-bottom flask and dissolved in 50 mL of anhydrous dichloromethane, and the resulting solution was cooled to 0° C. in an ice bath under an atmosphere of $N_2(g)$. Triethylamine (2.1 mL, 15.2 mmol) and hexanoyl chloride (0.78 mL, 5.56 mmol) were then added, and the reaction mixture was stirred at 0° C. for 1 h and at room temperature for another 2 h. The reaction mixture was then concentrated under reduced pressure, and the product was purified by column chromatography (silica, 50% v/v EtOAc in Hexanes) yielding 19 as a colorless oil (1.848 g, 91%).

$^1$H NMR (400 MHz, CDCl$_3$) δ=5.12 (br, s, 1H), 5.06 (br, s, 1H), 3.48-3.43 (m, 4H), 3.32-3.24 (m, 4H), 2.32 (t, J=7.6 Hz, 2H), 1.62 (quin, J=7.6 Hz, 2H), 1.43 (s, 18H), 1.34-1.26 (m, 4H), 0.90 (t, J=6.7 Hz, 3H); $^{13}$C NMR (100 MHz, CDCl$_3$) δ=174.7, 156.4, 156.0, 79.5, 79.2, 48.3, 45.6, 39.5, 39.2, 32.9, 31.5, 28.3, 25.0, 22.5, 13.9; HRMS (ESI) calculated for [C$_{20}$H$_{40}$N$_3$O$_5$]$^+$ (M+H$^+$) requires m/z=402.2963. found 402.2966.

O.

calculated for [C$_{14}$H$_{26}$Cl$_2$N$_3$O$_3$]$^+$ (M+H$^+$) requires m/z=354.1346. found 354.1342.

P.

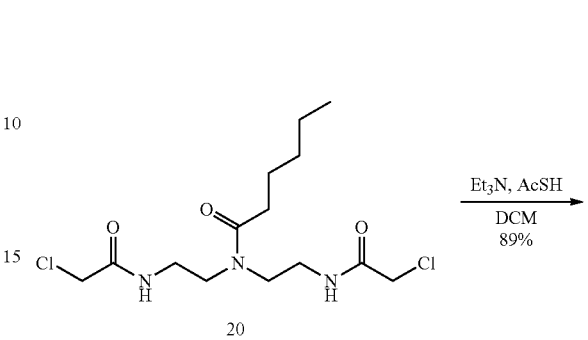

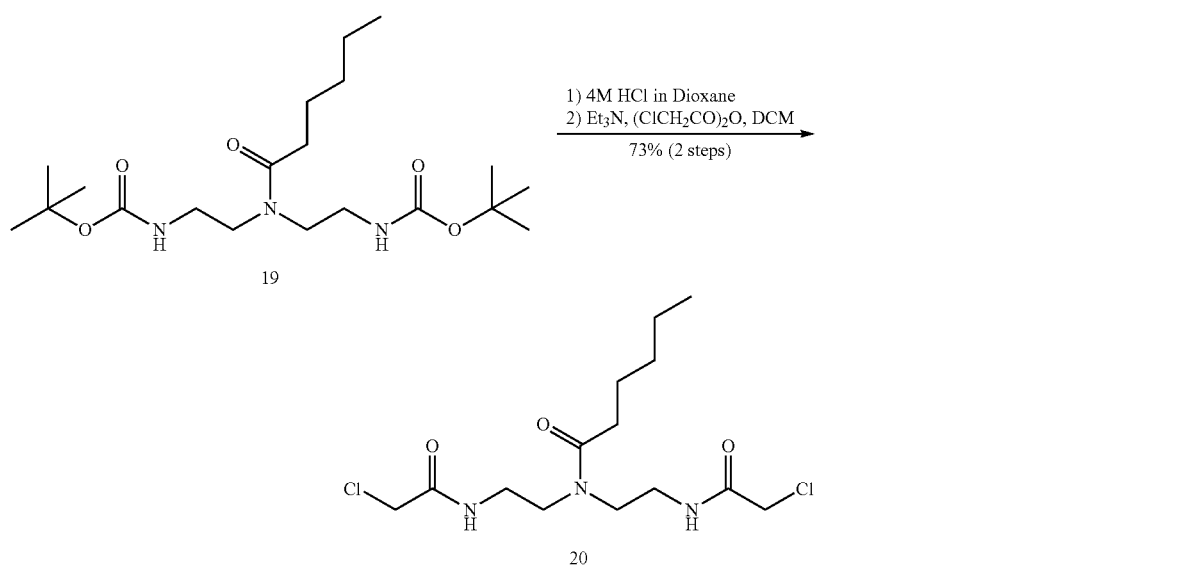

HCl (50 mL, 4M) in dioxane was added to a round-bottom flask containing 19 (0.867 g, 2.159 mmol). The resulting solution was stirred overnight and then concentrated under reduced pressure. The product was then partially dissolved in 40 mL of dichloromethane, and the resulting slurry was cooled to 0° C. in an ice bath and placed under an atmosphere of N$_2$(g). Triethylamine (1.8 mL, 12.9 mmol) and chloroacetic anhydride (0.923 g, 5.398 mmol) were then added, and the reaction mixture was stirred for 30 min before being quenched by the addition of 50 mL of saturated NaHCO$_3$(aq). The organic layer was extracted and washed with water (2×30 mL). The organic extract was then dried over MgSO$_4$(s), filtered, and concentrated under reduced pressure, and the product was purified by column chromatography (silica, 10% v/v methanol in dichloromethane), yielding 20 as a colorless oil (0.558 g, 73%).

$^1$H NMR (400 MHz, CDCl$_3$) δ=7.36 (br, s, 1H), 7.08 (br, s, 1H), 4.06 (s, 2H), 4.00 (s, 2H), 3.58 (t, J=6.1 Hz, 2H), 3.52-3.46 (m, 6H), 2.35 (t, J=7.4 Hz, 2H), 1.63 (quin, J=7.4 Hz, 2H), 1.34-1.26 (m, 4H), 0.90 (t, J=6.7 Hz, 3H); $^{13}$C NMR (100 MHz, CDCl$_3$) δ=175.2, 167.1, 166.9, 47.7, 45.3, 42.6, 39.7, 38.8, 33.1, 31.7, 25.3, 22.7, 14.1; HRMS (ESI)

-continued

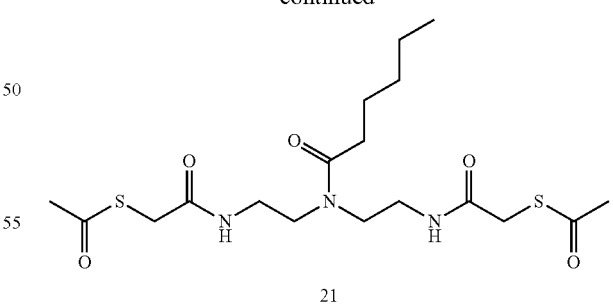

A round-bottom flask charged with 20 (0.558 g, 1.575 mmol) was dissolved with 20 mL of dichloromethane and placed under N$_2$(g). Triethylamine (1.1 mL, 7.9 mmol) and thioacetic acid (0.25 mL, 3.47 mmol) were then added, and the resulting solution was stirred under N$_2$(g). After 16 h, the reaction mixture was concentrated under reduced pressure, and the product was purified by column chromatography (silica, 10% v/v methanol in dichloromethane), providing 21 as a colorless oil (0.608 g, 89%).

¹H NMR (400 MHz, CDCl₃) δ=7.03-6.98 (m, 2H), 3.57 (s, 2H), 3.55 (s, 2H), 3.51-3.36 (m, 8H), 2.42 (s, 2H), 2.41 (s, 2H), 2.32 (t, J=7.4 Hz, 2H), 1.61 (quin, J=7.4 Hz, 2H), 1.36-1.28 (m, 4H), 0.90 (t, J=6.7 Hz, 3H); ¹³C NMR (100 MHz, CDCl₃) δ=195.7, 195.1, 175.2, 168.8, 168.6, 47.8, 45.3, 39.6, 38.9, 33.1, 33.0, 32.9, 31.6, 30.4, 30.3, 25.2, 22.6, 14.1; HRMS (ESI) calculated for $[C_{18}H_{32}N_3O_5S_2]^+$ (M+H⁺) requires m/z=434.1778. found 434.1780.

Q.

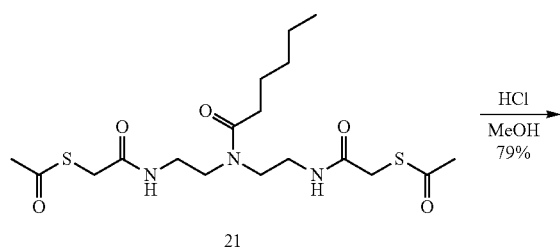

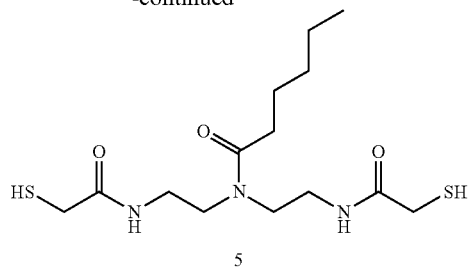

A flame-dried round-bottom flask was charged with 21 (0.149 g, 0.344 mmol) and placed under an atmosphere of N₂(g). Anhydrous methanol (6 mL) followed by 3 mL of 3 N HCl in methanol were then added, and the resulting solution was stirred under N₂(g). After 24 h, the reaction mixture was concentrated under reduced pressure, and the product was purified by reverse-phase HPLC using a preparatory C18 column and a linear gradient of 10-80% v/v acetonitrile (0.1% v/v TFA) in water (0.1% v/v TFA) over 45 min. Dithiol 5 eluted at 28 min and, after lyophilization, was isolated as a colorless oil (94.98 mg, 79%).

¹H NMR (400 MHz, DMSO-d₆) δ=8.21 (t, J=5.8 Hz, 1H), 8.07 (t, J=5.8 Hz, 1H), 3.31 (t, J=6.6 Hz, 2H), 3.29 (t, J=6.6 Hz, 2H) 3.22=3.15 (m, 4H), 3.08 (d, J=8.0 Hz, 2H), 3.06 (d, J=8.0 Hz, 2H), 2.75 (t, J=8.0 Hz, 1H), 2.72 (t, J=8.0 Hz, 1H), 2.27 (t, J=7.5 Hz, 2H), 1.48 (quin, J=7.5 Hz, 2H), 1.32-1.20 (m, 4H), 0.86 (t, J=6.9 Hz, 3H); ¹³C NMR (100 MHz, DMSO-d₆) δ=172.5, 170.0, 169.7, 46.8, 44.7, 37.8, 37.0, 32.0, 31.1, 27.2, 27.1, 24.6, 22.1, 14.0; HRMS (ESI) calculated for $[C_{14}H_{28}N_3O_3S_2]^+$ (M+H⁺) requires m/z=350.1567. found 350.1565.

R.

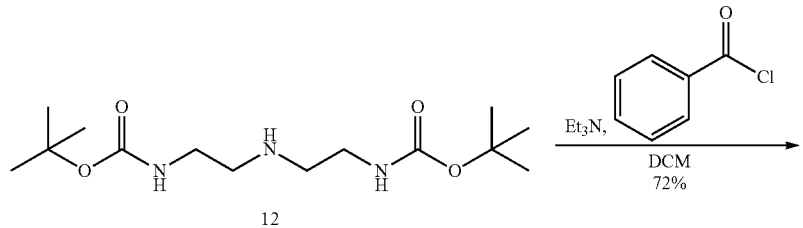

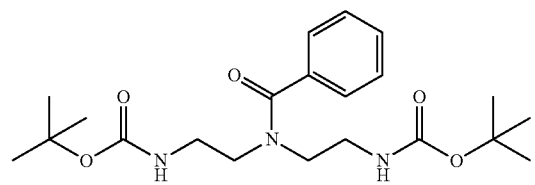

Compound 12 (1.391 g, 4.585 mmol) was placed in a flame-dried round-bottom flask and dissolved in 50 mL of anhydrous dichloromethane, and the resulting solution was cooled to 0° C. in an ice bath under an atmosphere of N$_2$(g). Triethylamine (1.9 mL, 13.8 mmol) and benzoyl chloride (0.64 mL, 5.50 mmol) were then added, and the resulting solution was stirred at 0° C. for 1 h and at room temperature for another 2 h. The reaction mixture was then concentrated under reduced pressure, and the product was purified by column chromatography (silica, EtOAc), yielding 22 as a colorless oil (1.848 g, 91%).

$^1$H NMR (400 MHz, CDCl$_3$) δ=7.40-7.35 (m, 5H), 5.12 (br, s, 1H), 5.06 (br, s, 1H), 3.67-3.24 (m, 8H), 1.44 (s, 18H); $^{13}$C NMR (100 MHz, CDCl$_3$) δ=173.4, 156.7, 155.8, 136.4, 129.6, 128.7, 126.8, 50.0, 45.0, 39.5, 38.9, 28.6, 28.4; HRMS (ESI) calculated for [C$_{21}$H$_{34}$N$_3$O$_5$]$^+$ (M+H$^+$) requires m/z=408.2493. found 408.2491.

S.

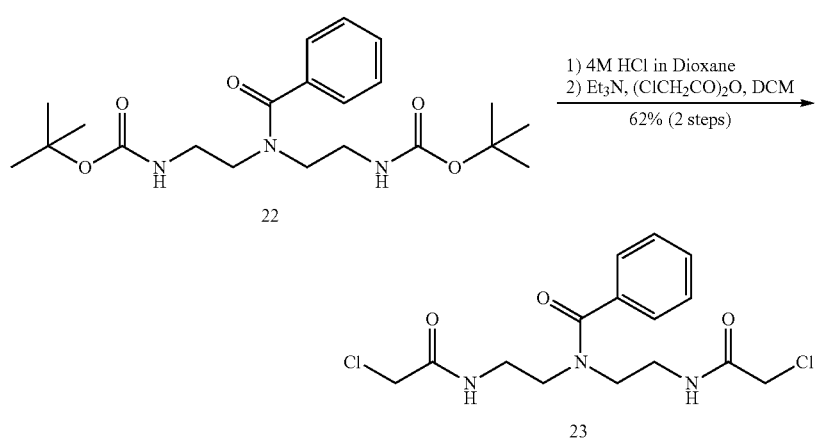

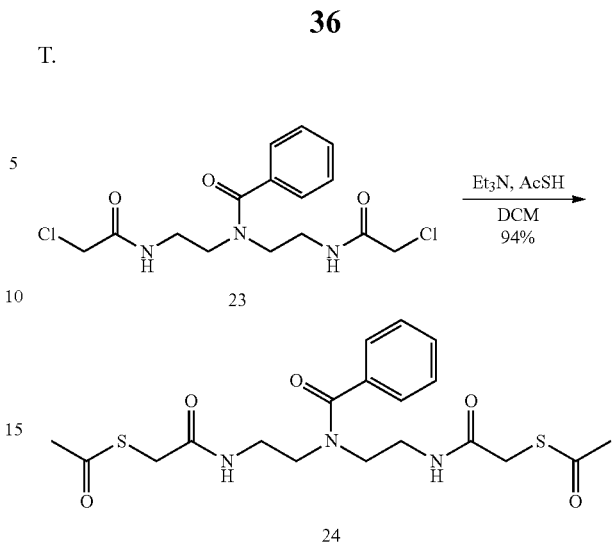

T.

HCl (50 mL, 4 M) in dioxane was added to a round-bottom flask containing 22 (0.713 g, 1.750 mmol). The resulting solution was stirred under N$_2$(g) overnight and then concentrated under reduced pressure. The product was then partially dissolved in 55 mL of dichloromethane, and the resulting slurry was cooled to 0° C. in an ice bath and placed under an atmosphere of N$_2$(g). Triethylamine (1.5 mL, 10.5 mmol) and chloroacetic anhydride (0.748 g, 4.375 mmol) were then added, and the reaction mixture was stirred for 30 min before being quenched by the addition of 55 mL of saturated NaHCO$_3$(aq). The organic layer was extracted and washed with water (2×40 mL). The organic extract was then dried with anhydrous MgSO$_4$(aq), filtered, and concentrated under reduced pressure, and the product was purified by column chromatography (silica, 10% v/v methanol in dichloromethane), yielding 23 as a colorless oil (0.391 g, 62%).

$^1$H NMR (400 MHz, CDCl$_3$) δ=7.44-7.41 (m, 3H), 7.37-7.35 (m, 2H), 6.90 (br, s, 2H), 4.05 (s, 2H), 3.98 (s, 2H), 3.80-3.41 (m, 8H); $^{13}$C NMR (100 MHz, CDCl$_3$) δ=173.4, 167.1, 166.3, 135.6, 129.9, 128.8, 126.5, 48.9, 44.6, 42.5, 39.0, 38.3; HRMS (ESI) calculated for [C$_{15}$H$_{20}$Cl$_2$N$_3$O$_3$]$^+$ (M+Na$^+$) requires m/z=360.0877. found 360.0888.

A round-bottom flask charged with 23 (0.391 g, 1.085 mmol) was dissolved with 15 mL of dichloromethane and placed under N$_2$(g). Triethylamine (0.76 mL, 5.43 mmol) and thioacetic acid (0.17 mL, 2.39 mmol) were then added, and the reaction was stirred under N$_2$(g). After 24 h, the reaction mixture was concentrated under reduced pressure, and the product was purified by column chromatography (silica, 10% v/v methanol in dichloromethane) providing 24 as a colorless oil (0.448 g, 94%).

$^1$H NMR (400 MHz, CDCl$_3$) δ=7.43-7.42 (m, 3H), 7.37-7.35 (m, 2H), 6.98 (br, s, 1H), 6.80 (br, s, 1H), 3.72-3.32 (m, 12H), 2.37 (s, 6H); $^{13}$C NMR (100 MHz, CDCl$_3$) δ=195.6, 195.4, 173.4, 168.9, 168.4, 135.8, 129.8, 128.6, 126.6, 49.3, 44.8, 39.2, 38.5, 32.9, 30.3; HRMS (ESI) calculated for [C$_{19}$H$_{26}$N$_3$O$_5$S$_2$]$^+$ (M+H$^+$) requires m/z=440.1309. found 440.1310.

U.

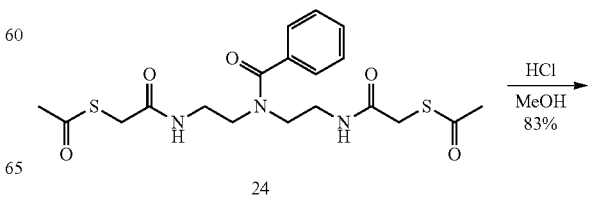

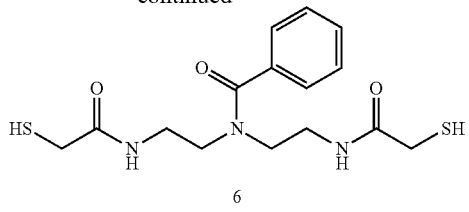

6

A flame-dried round-bottom flask was charged with 24 (0.131 g, 0.298 mmol) and placed under an atmosphere of $N_2(g)$. Anhydrous methanol (6 mL) followed by 3 mL of 3 N HCl in methanol was then added, and the resulting solution was stirred under $N_2(g)$. After 24 h, the reaction mixture was concentrated under reduced pressure, and the product was purified by reverse-phase HPLC using a preparatory C18 column and a linear gradient of 10-80% v/v acetonitrile (0.1% v/v TFA) in water (0.1% v/v TFA) over 45 min. Dithiol 6 eluted at 25 min and, after lyophilization, was isolated as a colorless oil (87.92 mg, 83%).

$^1$H NMR (400 MHz, DMSO-$d_6$) δ=8.23 (br, s, 1H), 8.08 (br, s, 1H), 7.42-7.40 (m, 3H), 7.36-7.34 (m, 2H), 3.52-3.50 (m, 2H), 3.36-3.34 (m, 2H), 3.28-3.25 (m, 2H), 3.14-3.10 (m, 4H), 3.01 (d, J=8.0 Hz, 2H), 2.76 (t, J=8.0 Hz, 1H), 2.68 (t, J=8.0 Hz, 1H); $^{13}$C NMR (100 MHz, DMSO-$d_6$) δ=171.1, 169.9, 169.6, 136.9, 129.0, 128.3, 126.6, 48.3, 44.1, 37.3, 36.7, 27.2, 27.0; HRMS (ESI) calculated for $[C_{15}H_{22}N_3O_3S_2]^+$ (M+H$^+$) requires m/z=356.1098. found 356.1096.

V.

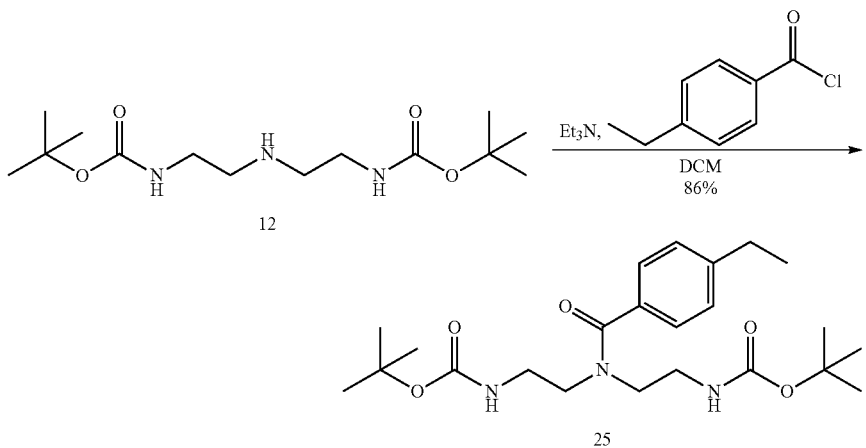

Compound 12 (1.592 g, 5.247 mmol) was placed in a flame-dried round-bottom flask and dissolved in 60 mL of anhydrous dichloromethane, and the resulting solution was cooled to 0° C. in an ice bath under an atmosphere of $N_2(g)$. Triethylamine (2.2 mL, 15.7 mmol) and 4-ethylbenzoyl chloride (0.93 mL, 6.30 mmol) were then added, and the resulting solution was stirred at 0° C. for 1 h and at room temperature for another 2 h. The reaction mixture was then concentrated under reduced pressure, and the product was purified by column chromatography (silica, 50% EtOAc v/v in hexanes), yielding 25 as a white solid (1.965 g, 86%).

$^1$H NMR (400 MHz, CDCl$_3$) δ=7.29 (d, J=7.7 Hz, 2H), 7.20 (d, J=7.7 Hz, 2H), 5.15 (br, s, 1H), 5.07 (br, s, 1H), 3.65-3.25 (m, 8H), 2.65 (q, J=7.6 Hz, 2H), 1.44 (2, 18H), 1.23 (t, J=7.6 Hz, 3H); $^{13}$C NMR (100 MHz, CDCl$_3$) δ=173.6, 156.6, 155.9, 133.7, 128.1, 126.9, 79.6, 50.0, 45.0, 39.4, 39.1, 28.8, 28.5, 15.4; HRMS (ESI) calculated for $[C_{23}H_{38}N_3O_5]^+$ (M+H$^+$) requires m/z=436.2806. found 436.2806.

W.

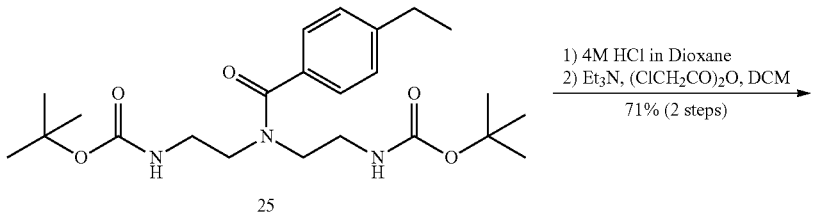

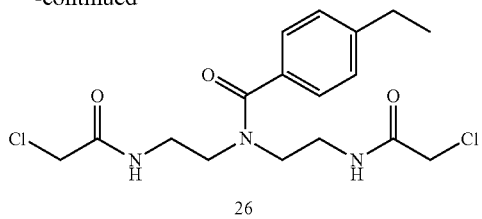

26

HCl (50 mL, 4M) in dioxane was added to a round-bottom flask containing 25 (0.689 g, 1.584 mmol). The resulting solution was stirred overnight and then concentrated under reduced pressure. The product was then partially dissolved in 60 mL of dichloromethane, and the resulting slurry was cooled to 0° C. in an ice bath and placed under an atmosphere of $N_2(g)$. Triethylamine (1.1 mL, 7.9 mmol) and chloroacetic anhydride (0.677 g, 3.960 mmol) were then added, and the reaction mixture was stirred for 30 min before being quenched by the addition of 60 mL of saturated $NaHCO_3(aq)$. The organic layer was extracted and washed twice with 40 mL of water. The organic extract was then dried with anhydrous $MgSO_4(s)$, filtered, and concentrated under reduced pressure, and the product was purified by column chromatography (silica, 10% v/v methanol in dichloromethane), yielding 26 as a colorless oil (0.437 g, 71%).

$^1$H NMR (400 MHz, $CDCl_3$) δ=7.61 (br, s, 1H), 7.28 (d, J=7.8 Hz, 2H), 7.23 (d, J=7.8 Hz, 2H), 7.10 (br, s, 1H), 3.97 (s, 4H), 3.73-3.41 (m, 8H), 2.67 (q, J=7.7 Hz, 2H), 1.24 (t, J=7.7 Hz, 3H); $^{13}$C NMR (100 MHz, $CDCl_3$) δ=173.6, 167.1, 166.5, 146.3, 132.9, 128.2, 126.7, 48.9, 44.6, 42.5, 38.5, 28.7, 15.4; HRMS (ESI) calculated for $[C_{17}H_{24}O_2N_3O_3]^+$ (M+H$^+$) requires m/z=388.1190. found 388.1192.

X.

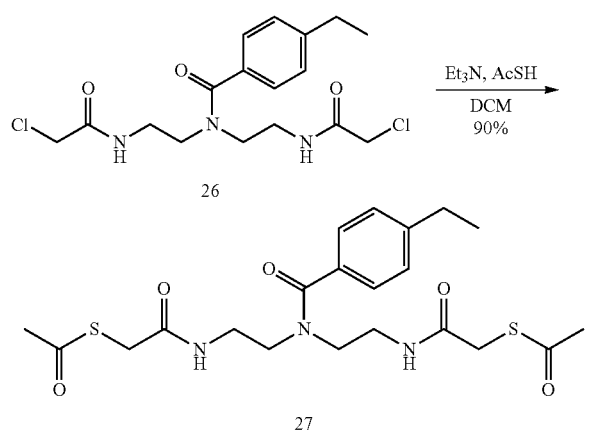

A round-bottom flask was charged with 26 (0.437 g, 1.125 mmol) dissolved in 15 mL of dichloromethane and placed under an atmosphere of $N_2(g)$. Triethylamine (0.78 mL, 5.62 mmol) and thioacetic acid (0.18 mL, 2.48 mmol) were then added, and the resulting solution was stirred under $N_2(g)$. After 24 h, the reaction mixture was concentrated under reduced pressure, and the product was purified by column chromatography (silica, 10% v/v methanol in dichloromethane), providing 27 as a yellow solid (0.473 g, 90%).

$^1$H NMR (400 MHz, $CDCl_3$) δ=7.29 (d, J=8.0 Hz, 2H), 7.23 (d, J=8.0 Hz, 2H), 7.02 (br, s, 1H), 6.84 (br, s, 1H), 3.68-3.33 (m, 12H), 2.68 (q, J=7.6 Hz, 2H), 2.37 (s, 6H), 1.25 (t, J=7.6 Hz, 3H); $^{13}$C NMR (100 MHz, $CDCl_3$) δ=195.6, 173.7, 169.0, 168.5, 146.3, 133.2, 128.2, 126.9, 49.5, 44.9, 39.3, 38.7, 33.0, 30.4, 28.8, 15.5; HRMS (ESI) calculated for $[C_{21}H_{30}N_3O_5S_2]^+$ (M+H$^+$) requires m/z=468.1622. found 468.1626.

Y.

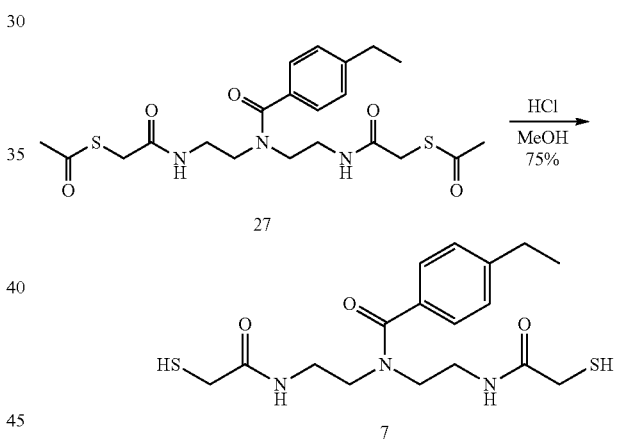

A flame-dried round-bottom flask was charged with 27 (0.147 g, 0.314 mmol) and placed under an inert atmosphere. Anhydrous methanol (6 mL) followed by 3 mL of 3 N HCl in methanol were then added, and the resulting solution was stirred under $N_2(g)$. After 24 h, the reaction mixture was concentrated under reduced pressure, and the product was purified by reverse-phase HPLC using a preparatory C18 column and a linear gradient of 10-80% v/v acetonitrile (0.1% v/v TFA) in water (0.1% v/v TFA) over 45 min. Dithiol 7 eluted at 30 min and, after lyophilization, was isolated as a white solid (90.32 mg, 75%).

$^1$H NMR (400 MHz, DMSO-$d_6$) δ=8.20 (br, s, 1H), 8.06 (br, s, 1H), 7.28 (d, J=7.8 Hz, 2H), 7.24 (d, J=7.8 Hz, 2H), 3.54-3.46 (m, 2H), 3.35-3.29 (m, 4H), 3.14-3.02 (m, 6H), 2.74-2.60 (m, 4H), 1.19 (t, J=7.5 Hz, 3H); $^{13}$C NMR (100 MHz, DMSO-$d_6$) δ=171.2, 169.8, 169.6, 144.6, 134.2, 127.6, 126.7, 48.4, 44.1, 37.3, 36.8, 28.0, 27.1, 15.4; HRMS (ESI) calculated for $[C_{17}H_{26}N_3O_3S_2]^+$ (M+Na$^+$) requires m/z=384.1411. found 384.1411.

Z.

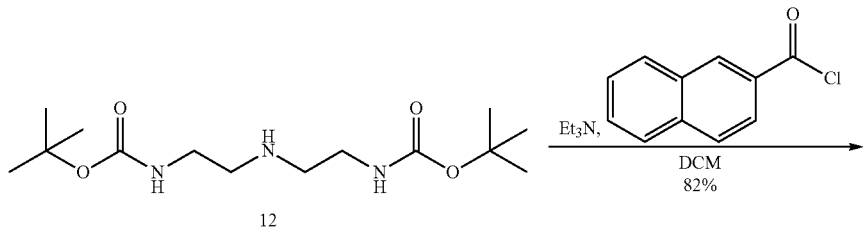

Compound 12 (0.203 g, 0.669 mmol) was placed in a flame-dried round-bottom flask and dissolved in 10 mL of anhydrous dichloromethane, and the resulting solution was cooled to 0° C. in an ice bath under an atmosphere of N₂(g). Triethylamine (0.28 mL, 2.01 mmol) and 2-naphthoyl chloride (0.153 g, 0.803 mmol) were then added, and the resulting solution was stirred at 0° C. for 1 h and at room temperature for another 2 h. The reaction mixture was then concentrated under reduced pressure, and the product was purified by column chromatography (silica, 50% EtOAc v/v in Hexanes), yielding 28 as a white solid (0.251 g, 82%).

$^1$H NMR (400 MHz, CDCl$_3$) δ=7.90-7.87 (m, 1H), 7.85-7.82 (m, 3H), 7.53-7.49 (m, 2H), 7.47-7.47 (d, J=8.5 Hz, 1H), 5.35 (br, s, 1H), 5.11 (br, s, 1H), 3.73-3.65 (m, 2H), 3.51-3.40 (m, 4H), 3.27-3.19 (m, 2H), 1.45 (s, 9H), 1.39 (s, 9H); $^{13}$C NMR (100 MHz, CDCl$_3$) δ=173.1, 156.6, 155.8, 133.6, 133.5, 132.7, 128.4, 127.8, 127.0, 126.7, 126.5, 124.1, 79.4, 49.9, 45.1, 39.2, 38.8, 28.5, 28.4; HRMS (ESI) calculated for [C$_{25}$H$_{36}$N$_3$O$_5$]$^+$ (M+Na$^+$) requires m/z=458.2650. found 458.2642.

AA.

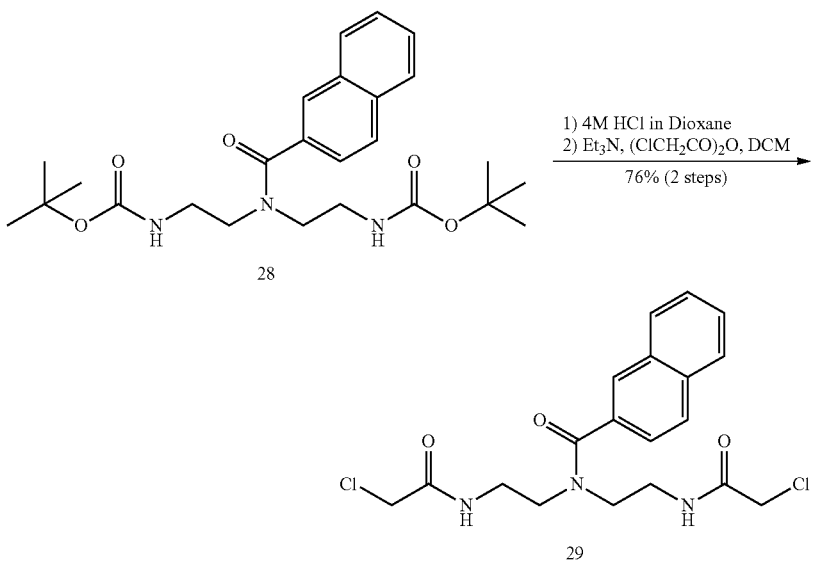

HCl (15 mL, 4 M) in dioxane was added to a round-bottom flask containing 28 (0.251 g, 0.549 mmol). The resulting solution was stirred overnight and then concentrated under reduced pressure. The product was then partially dissolved in 20 mL of dichloromethane, and the resulting slurry was cooled to 0° C. in an ice bath and placed under an atmosphere of N₂(g). Triethylamine (0.46 mL, 3.28 mmol) and chloroacetic anhydride (0.235 g, 1.373 mmol) were then added, and the reaction mixture was stirred for 30 min before being quenched by the addition of 20 mL of saturated NaHCO$_3$(aq). The organic layer was extracted and washed with water (2×10 mL). The organic extract was then dried over anhydrous MgSO$_4$(s), filtered, and concentrated under reduced pressure, and the product was purified by column chromatography (silica, 10% v/v methanol in dichloromethane), yielding 29 as a colorless oil (0.171 g, 76%).

$^1$H NMR (400 MHz, CDCl$_3$) δ=7.91-7.86 (m, 4H), 7.58-7.53 (m, 2H), 7.45-7.43 (m, 2H), 6.90 (br, s, 1H), 4.06-3.43 (m, 12H); $^{13}$C NMR (100 MHz, CDCl$_3$) δ=173.4, 167.1, 166.5, 133.6, 133.0, 132.7, 128.8, 128.4, 128.0, 127.4, 127.1, 126.5, 123.7, 49.0, 44.7, 42.6, 38.8, 38.4; HRMS (ESI) calculated for [C$_{19}$H$_{22}$O$_2$N$_3$O$_3$]$^+$ (M+Na$^+$) requires m/z=410.1033. found 410.1033.

BB.

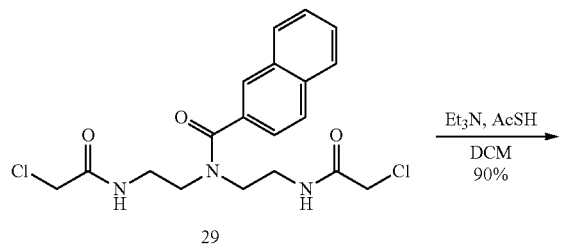

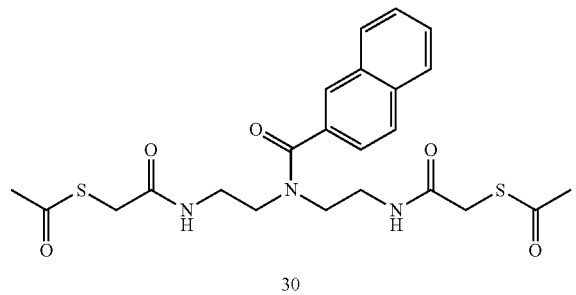

A round-bottom flask was charged with 29 (0.171 g, 0.417 mmol) dissolved in 5 mL of dichloromethane, and the resulting solution was placed under an atmosphere of N$_2$(g). Triethylamine (0.29 mL, 2.08 mmol) and thioacetic acid (0.1 mL, 1.40 mmol) were then added, and the resulting solution was stirred under N$_2$(g). After 24 h, the reaction mixture was concentrated under reduced pressure, and the product was purified by column chromatography (silica, 10% v/v methanol in dichloromethane), providing 30 as a yellow solid (0.184 g, 90%).

$^1$H NMR (400 MHz, CDCl$_3$) δ=7.87-7.82 (m, 4H), 7.53-7.49 (m, 2H), 7.44 (d, J=8.4 Hz, 1H), 7.35 (br, s, 1H), 7.10 (br, s, 1H), 3.69-3.28 (m, 12H), 2.30 (s, 6H); $^{13}$C NMR (100 MHz, CDCl$_3$) δ=195.5, 173.3, 168.9, 168.4, 133.5, 133.1, 132.6, 128.5, 127.9, 127.2, 126.9, 126.5, 123.9, 49.3, 44.8, 39.2, 38.5, 32.9, 30.3; HRMS (ESI) calculated for [C$_{23}$H$_{28}$N$_3$O$_5$S$_2$]$^+$ (M+Na$^+$) requires m/z=490.1465. found 490.1464.

CC.

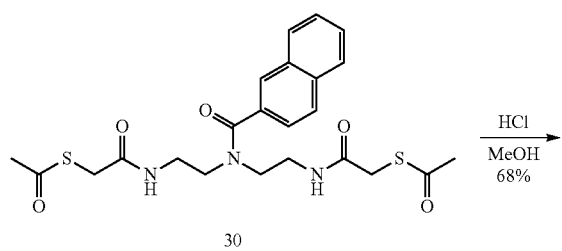

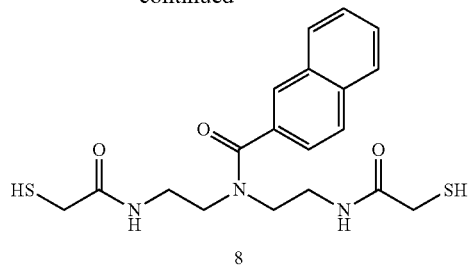

A flame-dried round-bottom flask was charged with 30 (0.184 g, 0.376 mmol) and placed under an atmosphere of N$_2$(g). Anhydrous methanol (6 mL) followed by 3 mL of 3 N HCl in methanol were then added, and the resulting solution was stirred under N$_2$. After 24 h, the reaction mixture was concentrated under reduced pressure, and the product was purified by reverse-phase HPLC using a preparatory C18 column and a linear gradient of 10-80% v/v acetonitrile (0.1% v/v TFA) in water (0.1% v/v TFA) over 45 min. Dithiol 8 eluted at 32 min and, after lyophilization, was isolated as a white solid (103.69 mg, 68%).

$^1$H NMR (400 MHz, DMSO-d$_6$) δ=8.29 (t, J=5.7 Hz, 1H), 8.06 (t, J=5.7 Hz, 1H), 7.97-7.93 (m, 4H), 7.59-7.55 (m, 2H), 7.50 (dd, J=8.5, 1.6 Hz, 1H), 3.59-3.57 (m, 2H), 3.43-3.34 (m, 4H), 3.16 (m, 4H), 3.00 (d, J=8.0 Hz, 2H), 2.80 (t, J=8.0 Hz, 1H), 2.66 (t, J=8.0 Hz, 1H); $^{13}$C NMR (100 MHz, DMSO-d$_6$) δ=171.1, 170.0, 169.7, 134.3, 132.9, 132.3, 128.3, 128.0, 127.8, 126.9, 126.7, 125.9, 124.5, 48.5, 44.2, 37.3, 36.8, 27.3, 27.1; HRMS (ESI) calculated for [C$_{19}$H$_{24}$N$_3$O$_3$S$_2$]$^+$ (M+Na$^+$) requires m/z=406.1254. found 406.1256.

Example 3

Determination of Thiol pK$_a$ Values

Figure 5:
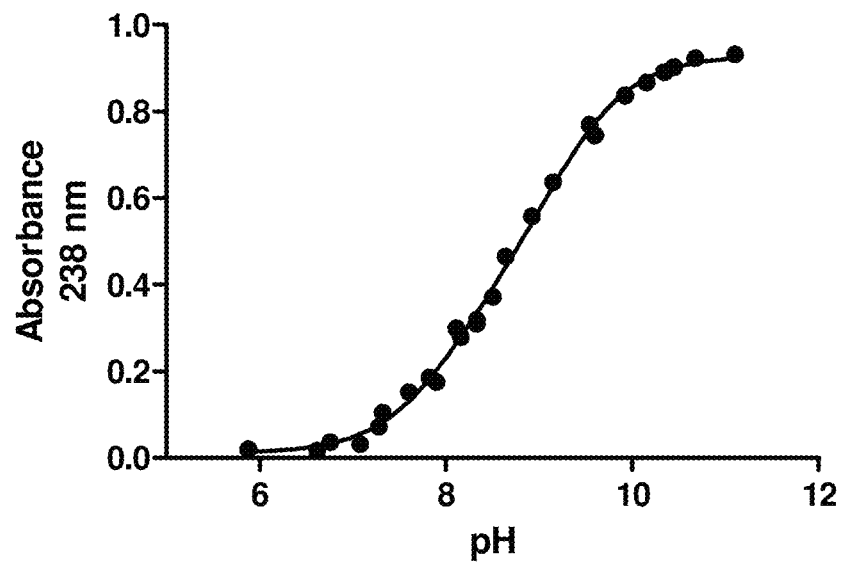
FIG. 5 is a graph showing the effect of pH on absorbance by compound 2 at 238 nm in 0.10 M potassium phosphate buffers. pKa values of 8.0±0.2 and 9.2±0.1, and extinction coefficients of $\epsilon_{SH}^{SH}$=9.20, $\epsilon_{SH}^{S-}$=3996, $\epsilon_{S-}^{S-}$=9296 M−1 cm−1 with $r^2$>0.99 were determined by fitting the data to eq 1.
Figure 6:
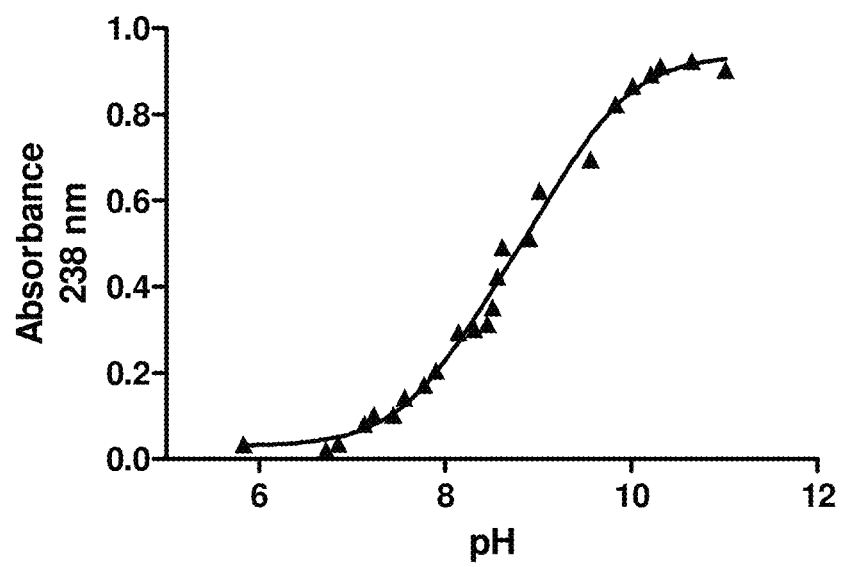
FIG. 6 is a graph showing the effect of pH on absorbance by compound 5 at 238 nm in 0.10 M potassium phosphate buffers. pKa values of 8.1±0.3 and 9.3±0.3, and extinction coefficients of $\epsilon_{SH}^{SH}$=10.23, $\epsilon_{SH}^{S-}$=4610, $\epsilon_{S-}^{S-}$9386 M−1 cm−1 with $r^2$>0.99 were determined by fitting the data to eq 1.
Figure 7:
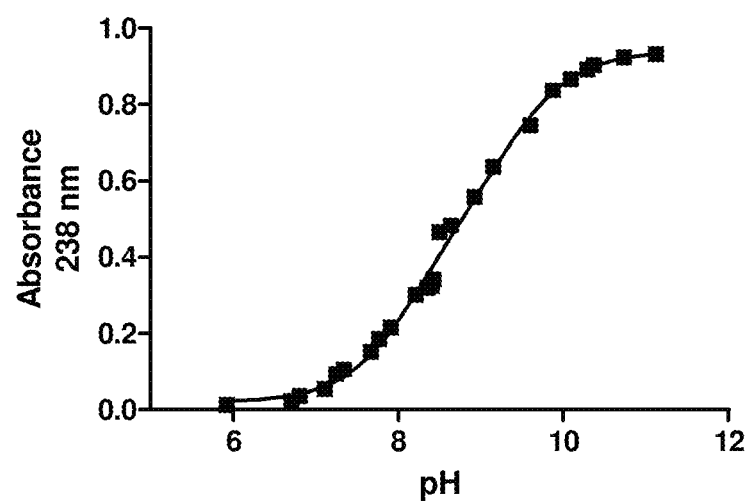
FIG. 7 is a graph showing the effect of pH on absorbance by 7 at 238 nm in 0.10 M potassium phosphate buffers. pKa values of 8.1±0.2 and 9.4±0.2, and extinction coefficients of $\epsilon_{SH}^{SH}$=8.13, $\epsilon_{SH}^{S-}$=4940, $\epsilon_{S-}^{S-}$=9390 M−1 cm−1 with $r^2$>0.99 were determined by fitting the data to eq 1.

The thiol pK$_a$ values for 2 and 7 were determined by closely following a procedure reported previously that exploits the elevated absorbance of the deprotonated thiolate at 238 nm. [72] Plots of A$_{238}$ vs pH were recorded (FIGS. 5 and 6), and pK$_a$ values were determined by fitting these data to eq 1, which was derived from Beer's law and the definition of the acid dissociation constant. [9, 55]

$$A_{238} = C_T \left( \frac{\varepsilon_{S-}^{S-} 10^{(pH-pKa2)} + \varepsilon_{SH}^{S-} + \varepsilon_{SH}^{SH} 10^{(pKa1-pH)}}{10^{(pH-pKa2)} + 1 + 10^{(pKa1-pH)}} \right) \quad (1)$$

In eq 1, $C_T$ is the total thiol concentration, $\epsilon_{SH}^{SH}$ is the extinction coefficient of the doubly protonated form of 2 or 7, $\epsilon_{SH}^{S-}$ is the extinction coefficient of the singly protonated form of 2 or 7, and $\epsilon_{S-}^{S-}$ is the extinction coefficient of the doubly deprotonated form of 2 or 7.

Example 4

Determination of Disulfide E$^{o\prime}$ Values

The reduction potentials of BMC, 2, and 7 were determined as described previously. [56, 9, 55] Briefly, an equilibrium was established between reduced BMC (or 2, 5, or 7) and βME$^{OX}$, and analyzed with analytical HPLC. The equilibrium concentrations were determined by integration of the peaks corresponding to βME and βME$^{ox}$. From these concentrations, the K$_{eq}$ for the reaction was determined and the reduction potential of BMC (or 2 or 7) was then calculated using the Nernst equation and E$_{βME}^{OX_o'}$=−0.260 V. The values reported are the mean (±SE) of three separate measurements for each compound Example 5

Assay for Disulfide-Bond Isomerization Activity sRNase was prepared as described previously [73], and validated by its having low ribonucleolytic activity and few free thiols according to Ellman's assay. Bovine liver PDI was from Sigma-Aldrich (product #P3818). The activation of sRNase A in the presence of refolding catalysts was determined as described previously. [9] Refolding reactions were performed at 30° C. in 50 mM Tris-HCl buffer, pH 7.6, containing GSH (1.0 mM), GSSG (0.2 mM), and catalyst (1.0 mM). Organocatalysts were delivered from 100-fold concentrated stock solutions in DMSO. Reactions were initiated by the addition of sRNase A to a final concentration of 5 μg/mL. Reaction progress was monitored by quantifying the cleavage of the substrate 6-FAM-dArUdAdA-6-TAMRA at 493/515 nm, as described previously. [58] Assays were performed in triplicate at ambient temperature in a black polystyrene 96-well plate, in 200 μL of 0.10 M MES-NaOH buffer, pH 6.0, containing NaCl (0.10 M). The resulting fluorescence data were fitted to the equation $k_{cat}/K_M=(\Delta I/\Delta t)/(I_f-I_0)[E]$, in which $\Delta I/\Delta t$ is the initial reaction velocity, $I_0$ is the fluorescence intensity before addition of any ribonuclease, $I_f$ is the fluorescence intensity after complete substrate hydrolysis, and [E] is the total ribonuclease concentration. Reaction progress was monitored every hour until the increase in activity leveled off (~5 h). In FIG. 4A, data were fitted to eq 2. [30]

$$[\text{active RNase } A] = [s\text{RNase } A]_{t=0}(1 - e^{[catalyst]tk_{obs}}) \quad (2)$$

REFERENCES

1. Jocelyn, P. C., Ed. *Biochemistry of the SH Group: The Occurence, Chemical Properties, Metabolism and Biological Function of Thiols and Disulfides*: London, U.K., 1972.
2. Buchner, J.; Moroder, L., Eds. *Oxidative Folding of Peptides and Proteins*; The Royal Society of Chemistry: Cambridge, UK, 2009.
3. Lindahl, M.; Mata-Cabana, A.; Kieselbach, T. *Antioxid. Redox Signal.* 2011, 14, 2581-642.
4. Oka, O. B.; Bulleid, N. J. *Biochim. Biophys. Acta* 2013, 1833, 2425-2429.
5. Anfinsen, C. B. *Science* 1973, 181, 223-230.
6. Robinson, A. S.; Hines, V.; Wittrup, K. D. *Biotechnology* 1994, 12, 381-384.
7. Laboissière, M. C. A.; Sturley, S. L.; Raines, R. T. *J. Biol. Chem.* 1995, 270, 28006-28009.
8. Guzman, N. A., Ed. *Prolyl Hydroxylase, Protein Disulfide Isomerase, and Other Structurally Related Proteins*; Marcel Dekker: New York, N.Y., 1998.
9. Woycechowsky, K. J.; Raines, R. T. *Curr. Opin. Chem. Biol.* 2000, 4, 533-539.
10. Freedman, R. B.; Klappa, P.; Ruddock, L. W. *EMBO Rep.* 2002, 3, 136-140.
11. Kersteen, E. A.; Raines, R. T. *Antioxid. Redox Signal.* 2003, 5, 413-424.
12. Tian, G.; Xiang, S.; Noiva, R.; Lennarz, W. J.; Schindelin, H. *Cell* 2006, 124, 61-73.
13. Gruber, C. W.; Cemazar, M.; Heras, B.; Martin, J. L.; Craik, D. J. *Trends Biochem. Sci.* 2006, 31, 455-464.
14. Denisov, A. Y.; Maattanen, P.; Dabrowski, C.; Kozlov, G.; Thomas, D. Y.; Gehring, K. *FEBS J.* 2009, 276, 1440-1449.
15. Kersteen, E. A.; Barrows, S. R.; Raines, R. T. *Biochemistry* 2005, 44, 12168-12178.
16. Holmgren, A. *J. Biol. Chem.* 1979, 254, 9627-9632.
17. Edman, J. C.; Ellis, L.; Blacher, R. W.; Roth, R. A.; Rutter, W. J. *Nature* 1985, 317, 267-270.
18. Darby, N. J.; Creighton, T. E. *Biochemistry* 1995, 34, 3576-3587.
19. Gilbert, H. F. *Adv. Enzymol.* 1990, 63, 69-172.
20. Chivers, P. T.; Prehoda, K. E.; Raines, R. T. *Biochemistry* 1997, 36, 4061-4066.
21. Hawkins, H. C.; Freedman, R. B. *Biochem. J.* 1991, 275, 335-339.
22. Lundstrom, J.; Holmgren, A. *Biochemistry* 1993, 32, 6649-6655.
23. Hwang, C.; Sinskey, A. J.; Lodish, H. F. *Science* 1992, 257, 1496-1502.
24. Chivers, P. T.; Laboissière, M. C. A.; Raines, R. T. *EMBO J.* 1996, 15, 2659-2667.
25. Walker, K. W.; Lyles, M. M.; Gilbert, H. F. *Biochemistry* 1996, 35, 1972-1980.
26. Walker, K. W.; Gilbert, H. F. *J. Biol. Chem.* 1997, 272, 8845-8848.
27. Raines, R. T. *Chem. Rev.* 1998, 98, 1045-1066.
28. Lyles, M. M.; Gilbert, H. F. *Biochemistry* 1991, 30, 619-625.
29. Lees, W. J. *Curr. Opin. Chem. Biol.* 2008, 12, 740-5.
30. Woycechowsky, K. J.; Wittrup, K. D.; Raines, R. T. *Chem. Biol.* 1999, 6, 871-879.
31. Willis, M. S.; Hogan, J. K.; Prabhakar, P.; Liu, X.; Tsai, K.; Wei, Y.; Fox, T. *Protein Sci.* 2005, 14, 1818-1826.
32. Woycechowsky, K. J.; Hook, B. A.; Raines, R. T. *Biotechnol. Progr.* 2003, 19, 1307-1314.
33. Woycechowsky, K. J.; Raines, R. T. *Biochemistry* 2003, 42, 5387-5394.
34. Gough, J. D.; Gargano, J. M.; Donofrio, A. E.; Lees, W. J. *Biochemistry* 2003, 42, 11787-11797.
35. Gough, J. D.; Lees, W. J. *J. Biotechnol.* 2005, 115, 279-290.
36. Gough, J. D.; Lees, W. J. *Bioorg. Med. Chem.* 2005, 15, 777-781.
37. Gough, J. D.; Barrett, E. J.; Silva, Y.; Lees, W. J. *J. Biotechnol.* 2006, 125, 39-47.
38. Beld, J.; Woycechowsky, K. J.; Hilvert, D. *Biochemistry* 2008, 47, 6985-6987.
39. Beld, J.; Woycechowsky, K. J.; Hilvert, D. *Biochemistry* 2009, 48, 4662-4662.
40. Beld, J.; Woycechowsky, K. J.; Hilvert, D. *J. Biotechnol.* 2010, 150, 481-489.
41. Wang, G. Z.; Dong, X. Y.; Sun, Y. *Biochem. Eng. J.* 2011, 55, 169-175.
42. Patel, A. S.; Lees, W. J. *Bioorg. Med. Chem.* 2012, 20, 1020-1028.
43. Lees, W. J. *Chem Bio Chem* 2012, 13, 1725-1727.
44. Jencks, W. R. *Catalysis in Chemistry and Enzymology*; New York, N.Y.: McGraw-Hill, 1969.
45. Shouldice, S. R.; Heras, B.; Walden, P. M.; Totsika, M.; Schembri, M. A.; Martin, J. L. *Antioxid. Redox Signal.* 2011, 14, 1729-1760.

46. Kober, F. X.; Koelmel, W.; Kuper, J.; Drechsler, J.; Mais, C.; Hermanns, H. M.; Schindelin, H. *J. Biol. Chem.* 2013, 288, 2029-2039.
47. Lins, L.; Brasseur, R. *FASEB J.* 1995, 9, 535-540.
48. Knowles, J. R.; Parsons, C. A. *Chem. Commun.* 1967, 755-757.
49. Blyth, C. A.; Knowles, J. R. *J. Am. Chem. Soc.* 1971, 93, 3017-3021.
50. Knowles, J. R.; Parsons, C. A. *Nature* 1969, 221, 5553-54.
51. Blyth, C. A.; Knowles, J. R. *J. Am. Chem. Soc.* 1971, 93, 3021-3027.
52. Wang, G. Z.; Dong, X. Y.; Sun, Y. *Biotechnol. Progr.* 2011, 27, 377-385.
53. Liu, H.; Dong, X. Y.; Sun, Y. *Biochem. Eng. J.* 2013, 79, 29-32.
54. Lees, W. J.; Singh, R.; Whitesides, G. M. *J. Org. Chem.* 1991, 56, 7328-7331.
55. Lukesh, J. C.; Palte, M. J.; Raines, R. T. *J. Am. Chem. Soc.* 2012, 134, 4057-4059.
56. Lamoureux, G. V.; Whitesides, G. M. *J. Org. Chem.* 1993, 58, 633-641.
57. Knowles, J. R. *Science* 1987, 236, 1252-1258.
58. Kelemen, B. R.; Klink, T. A.; Behlke, M. A.; Eubanks, S. R.; Leland, P. A.; Raines, R. T. *Nucleic Acids Res.* 1999, 27, 3696-3701.
59. Sangster, J. *J. Phys. Chem. Ref. Data* 1989, 18, 1111-1227.
60. Hansen, D. E.; Raines, R. T. *J. Chem. Educ.* 1990, 67, 483-489.
61. Guddat, L. W.; Bardwell, J. C.; Zander, T.; Martin, J. L. *Protein Sci.* 1997, 6, 1148-1156.
62. Gilbert, H. F. *J. Biol. Chem.* 1997, 272, 29399-29402.
63. Fernandes, P. A.; Ramos, M. *J. Chem. Eur. J.* 2004, 10, 257-266.
64. Marston, F. A. O. *Biochem. J.* 1986, 240, 1-12.
65. De Bernardez Clark, E. *Curr. Opin. Biotechnol.* 1998, 9, 157-163.
66. Martelli, P. L.; Fariselli, P.; Casadio, R. *Proteomics* 2004, 4, 1665-1671.
67. Fahey, R. C.; Hunt, J. S.; Windham, G. C. *J. Mol. Evol.* 1977, 10, 155-160.
68. Thorton, J. M. *J. Mol. Biol.* 1981, 151, 261-287.
69. Liu, H.; May, K. *mAbs* 2012, 4, 17-23.
70. Pharmaceutical Research and Manufacturers of America report "Medicines in Development—Biologics, 2013 Report".
71. A. P. Umali, H. L. Crampton and E. E. Simanek, *J. Org. Chem.*, 2007, 72, 9866-9874.
72. R. E. Benesch and R. Benesch, *J. Am. Chem. Soc.*, 1955, 77, 5877-5881.
73. A. de Crouy-Chanel, M. Kohiyama and G. Richarme, *J. Biol. Chem.*, 1995, 270, 22669-22672.
74. Rudolph R. and Lilie, H. (1996). In vitro folding of inclusion body proteins. FASEB 10:49-56.
75. Lilie, H., et al. (1998). Advances in refolding of proteins produced in *E. coli*. Curr. Opin. in Biotech. 9:497-501.
76. Middelberg, A. (2002). Preparative protein refolding. Trends Biotechnol. 20(10):437-443.
77. Hevehan, D. L. and Clark, E. D. B. (1997). Oxidative renaturation of lysozyme at high concentrations. Biotechnol. Bioeng. 54(3):221-230.
78. Mannhold, R. et al. (March 2009) J. Pharmaceutical Sciences 98(3):861-893.
79. Vallejo, L. F. et al. (2004). Strategies for the recovery of active proteins through refolding of bacterial inclusion body proteins. Microbial Cell Factories 3:11 (12 pages).
80. Goldberg M E, Expert-Bezançon N, Vuillard L, Rabilloud T: Nondetergent sulphobetaines: A new class of molecules that facilitate in vitro renaturation. Folding & Design 1995, 1:21-27.
81. Vicik S M: Methods of refolding proteins by use of zwitterionic low molecular weight agents. 1999 WO 99/18196.
82. Vallejo L F, Brokelmann M, Marten S, Trappe S, Cabrera-Crespo J, Hoffmann A, Gross G, Weich H A, Rinas U: Renaturation and purification of bone morphogenetic protein-2 produced as inclusion bodies in high-cell-density cultures of recombinant *Escherichia coli*. J Biotechnol 2002, 94:185-194.
83. A. Blum, J. Bottcher, B. Sammet, T. Luksch, A. Heine, G. Klebe and W. E. Diederich, Achiral Oligoamines as Versatile Tool for the Development of Aspartic Protease Inhibitors Bioorg. Med. Chem., 2008, 16, 8574-8586.
84. T. A. Klink, K. J. Woycechowsky, K. M. Taylor and R. T. Raines, Eur. J. Biochem., 2000, 267, 566-572.
85. A. Mullard, Nat. Rev. Drug Discov., 2013, 12, 329-332.

We claim:

1. A compound having formula I:

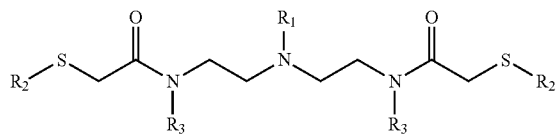

where:
$R_1$ is hydrogen or a —CO—$R_4$ group, where $R_4$ is an optionally substituted aliphatic group or an optionally substituted aryl group;

each $R_2$ is independently hydrogen or a —CO—$R_5$ group, where $R_5$ is an alkyl group having 1-8 carbon atoms, an alkenyl group having 3-8 carbon atoms, a phenyl group, a benzyl group, a phenethyl group or a naphthyl group; and each $R_3$ is independently hydrogen or an alkyl group having 1-3 carbon atoms; wherein substituents for $R_4$, if present, are selected from halogens, alkyl groups having 1-6 carbon atoms, alkoxy groups having 1-6 carbon atoms and aryl groups having 6-12 carbon atoms.

2. The compound of claim 1, wherein the calculated log P of the compound $(CH_3)_2NR_1$ is greater than or equal to 0.

3. The compound of claim 1, wherein each $R_2$ and each $R_3$ are hydrogens.

4. The compound of claim 1, wherein $R_1$ is —$COR_4$.

5. The compound of claim 4, wherein $R_4$ is an alkyl group having 1-20 carbon atoms or an alkenyl group having 3-20 carbon atoms.

6. The compound of claim 4, wherein $R_4$ is an alkyl group having 1-6 carbon atoms.

7. The compound of claim 4, wherein $R_4$ is an aryl group having 6-12 carbon atoms.

8. The compound of claim 4, wherein $R_4$ is a cyclopentyl, cyclohexyl, cyclooctyl, cyclononyl, cyclodecyl, cyclopentenyl, cyclohexenyl, cyclooctenyl, cyclononenyl or cyclodecenyl group.

9. The compound of claim 4, wherein $R_4$ is an optionally substituted phenyl, benzyl, biphenyl, naphthyl, indanyl or indenyl group.

10. The compound of claim 4, wherein $R_4$ is an alkyl-substituted phenyl group.

11. The compound of claim 1, wherein $R_1$, each $R_2$ and each of $R_3$ are hydrogens.

12. The compound of claim 1, wherein each $R_2$ and each of $R_3$ are hydrogens and $R_1$ is —$COR_4$, where $R_4$ is an unsubstituted straight-chain or branched alkyl group having 3-6 carbon atoms.

13. The compound of claim 1, wherein each $R_2$ and each of $R_3$ are hydrogens and $R_1$ is —$COR_4$, where $R_4$ is an unsubstituted phenyl group, an unsubstituted benzyl group, an unsubstituted phenethyl group, or an alkyl-susbstituted phenyl group.

14. The compound of claim 1, wherein each $R_2$ and each of $R_3$ are hydrogens and $R_1$ is —$COR_4$, where $R_4$ is an unsubstituted cycloalkyl group having 5-8 carbon atoms.

15. The compound of claim 1, wherein each $R_2$ is —$COR_5$.

16. The compound of claim 1, wherein each $R_2$ is —$COR_5$, each $R_3$ is hydrogen and $R_1$ is —$COR_4$.

17. A refolding buffer comprising one or more compounds of claim 1.

18. A method for forming a disulfide bond in a polypeetide or protein containing at least two cysteines which comprises contacting the polypeptide or protein with one or more catalysts of claim 1.

19. A method for isomerizing disulfide bonds in a polypeptide or protein containing at least two disulfide bonds which comprises contacting the polypeptide or protein with one or more catalysts of any of claim 1.

20. The compound of claim 1, wherein each $R_2$ and each $R_3$ are hydrogens and $R_1$ is a —CO—$R_4$ group, where $R_4$ is unsubstituted phenyl or a 4-ethyl phenyl group.

21. The compound of claim 1, wherein each $R_3$ is hydrogen, each $R_2$ is —$COR_5$, where $R_5$ is an alkyl group having 1-3 carbon atoms.

22. The compound of claim 1, which is

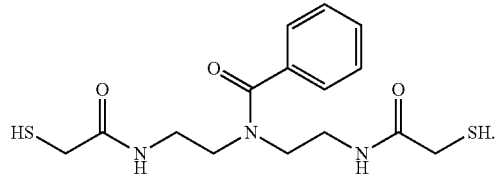

6

23. The compound of claim 1, which is

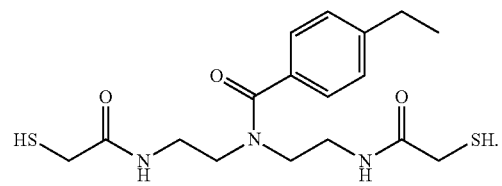

7

24. A refolding buffer of claim 17 comprising one or both of

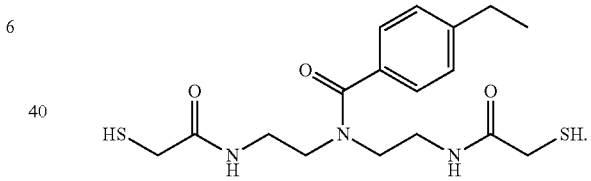

6 or

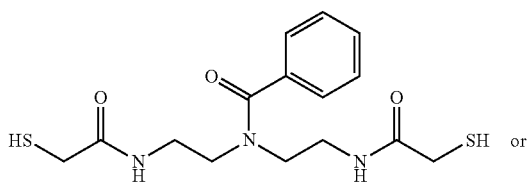

7

* * * * *